United States Patent [19]
Angst et al.

[11] Patent Number: 5,051,413
[45] Date of Patent: Sep. 24, 1991

[54] UNSATURATED AMINO ACIDS

[75] Inventors: Christof Angst, Menlo Park, Calif.; Derek E. Brundish, Horsham, England; John G. Dingwall, Nuglar; Graham E. Fagg, Riehen, both of Switzerland; Hans Allgeier, Lörrach-Haagen, Fed. Rep. of Germany; Guido Bold, Gipf-Oberfrick, Switzerland; Rudolf Duthaler, Bettingen, Switzerland; Roland Heckendorn; Antonio Togni, both of Arlesheim, Switzerland

[73] Assignee: Ciba-Geigy Corporation, Ardsley, N.Y.

[21] Appl. No.: 452,995

[22] Filed: Dec. 18, 1989

Related U.S. Application Data

[63] Continuation-in-part of Ser. No. 226,356, Jul. 29, 1988, abandoned, which is a continuation-in-part of Ser. No. 13,766, Feb. 12, 1987, abandoned.

[30] Foreign Application Priority Data

Feb. 13, 1986 [CH] Switzerland .......................... 578/86
Aug. 4, 1987 [CH] Switzerland .......................... 2986/87

[51] Int. Cl.⁵ .................... C07F 9/30; C07F 9/38; C07F 9/40; A61K 31/66
[52] U.S. Cl. .................... 514/119; 514/114; 562/11; 558/169; 558/170; 558/173; 558/174; 558/175; 560/172
[58] Field of Search .................. 562/11; 514/114, 119; 560/172; 558/169, 170, 173–175

[56] References Cited

U.S. PATENT DOCUMENTS

| | | | |
|---|---|---|---|
| 4,399,287 | 8/1983 | Baillie et al. | 548/119 |
| 4,477,391 | 10/1984 | Collins | 260/502.5 |
| 4,483,853 | 11/1984 | Collins et al. | 424/211 |
| 4,657,899 | 4/1987 | Rzeszotarski et al. | 514/120 |
| 4,776,875 | 10/1988 | Löher et al. | 71/86 |

FOREIGN PATENT DOCUMENTS

| | | |
|---|---|---|
| 3609818 | 9/1987 | Fed. Rep. of Germany . |
| 87314 | 8/1978 | Japan . |
| 8706131 | 10/1987 | PCT Int'l Appl. . |

OTHER PUBLICATIONS

Agr. Biol. Chem. 40, 1905–1906 (1976).
Agr. Biol. Chem. 41, 573–579 (1977).
Pol. J. Pharmacol. Pharm. 37, 575–584 (1985).
WO87/06131, 10/22/87.

*Primary Examiner*—J. E. Evans
*Attorney, Agent, or Firm*—JoAnn Villamizar

[57] ABSTRACT

The invention relates to unsaturated amino acids of the formula I

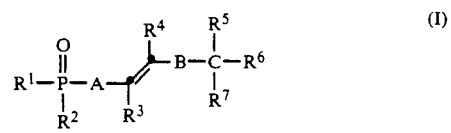

in which $R^1$ represents hydroxy or etherified hydroxy, $R^2$ represents hydrogen, alkyl, hydroxy or etherified hydroxy, $R^3$ represents hydrogen, alkyl, haloalkyl, hydroxyalkyl, lower alkoxyalkyl, arylalkyl, lower alkenyl, halogen or aryl, $R^4$ represents hydrogen, alkyl or aryl, $R^5$ represents hydrogen or alkyl, $R^6$ represents carboxy or esterified or amidated carboxy, $R^7$ represents amino or amino substituted by alkyl or acyl, A represents unsubstituted or alkyl-substituted α,ω-alkylene having from 1 to 3 carbon atoms or represents a bond, and B represents methylene or a bond, with the proviso that A is other than a bond when B represents a bond, and salts thereof. They can be manufactured, for example, in accordance with the Michaelis-Arbuzov reaction and can be used as pharmacologically active substances.

13 Claims, No Drawings

UNSATURATED AMINO ACIDS

This is a continuation-in-part of U.S. patent application Ser. No. 226,356, filed July 29, 1988, now abandoned, which in turn is a continuation-in-part of U.S. patent application Ser. No. 013,766, filed Feb. 12, 1987, now abandoned.

The invention relates to novel unsaturated amino acids, salts thereof, processes for the manufacture of these novel substances, pharmaceutical preparations containing these substances and the use of these substances and of preparations containing them.

The compounds according to the invention are compounds of the formula I

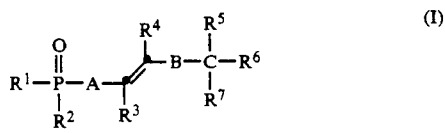

in which $R^1$ represents hydroxy or etherified hydroxy, $R^2$ represents hydrogen, alkyl, hydroxy or etherified hydroxy, $R^3$ represents hydrogen, alkyl, haloalkyl, hydroxyalkyl, lower alkoxyalkyl, arylalkyl, lower alkenyl, halogen or aryl, $R^4$ represents hydrogen, alkyl or aryl, $R^5$ represents hydrogen or alkyl, $R^6$ represents carboxy or esterified or amidated carboxy, $R^7$ represents amino or amino substituted by alkyl, aralkyl or acyl, A represents unsubstituted or alkyl-substituted $\alpha,\omega$-alkylene having from 1 to 3 carbon atoms or represents a bond, and B represents methylene or a bond, with the proviso that A is other than a bond when B represents a bond, and salts thereof.

The compounds of the formula I contain at least one chiral centre and may be in the form of enantiomers or enantiomeric mixtures, such as racemates, and if they contain more than one chiral centre, they may also be in the form of diastereoisomers or diastereoisomeric mixtures.

The carbon-carbon double bond of the compounds according to the invention is in the trans-configuration in relation to $R^3$ and $R^4$, or in relation to A and B, that is to say the compounds of the formula I are compounds of the E-series.

Compounds of the formula I in which $R^2$ represents hydrogen are phosphonous acids, those in which $R^2$ represents alkyl are phosphinic acids, and those in which $R^2$ represents hydroxy are phosphonic acids. In the names of the compounds of the formula I that are to be regarded as substituted carboxylic acids the prefixes "phosphino" ($R^2$ represents hydrogen), "phosphonyl" ($R^2$ represents alkyl) and "phosphono" ($R^2$ represents hydroxy) are used. Within the scope of this invention, alkyl is a saturated aliphatic hydrocarbon radical having, for example, up to 12 carbon atoms, but especially having up to 8 carbon atoms, the latter range also being represented by the term lower alkyl. $\alpha,\omega$-Alkylene having from 1 to 3 carbon atoms is methylene, 1,2-ethylene or 1,3-propylene $\alpha,\omega$-Alkylene substituted by alkyl is substituted at any position. Thus, methylene substituted by alkyl is, for example, 1,1-ethylene, 1,1-butylene or 1,1-octylene, 1,2-ethylene substituted by alkyl is, for example, 1,2-propylene, 1,2-butylene, 2,3-butylene, 1,2-pentylene or 1,2-nonylene, and 1,3-propylene substituted by alkyl is, for example, 1,3-butylene, 1,3-pentylene or 1,3-decylene.

Amino $R^7$ substituted by acyl may be acylamino or diacylamino. Amino $R^7$ substituted by alkyl is mono- or di-lower alkylamino.

In a corresponding acylamino group acyl is, for example, the acyl radical of an organic acid having, for example, up to 18 carbon atoms, especially an alkanecarboxylic acid optionally substituted, for example, by halogen, amino or phenyl, or benzoic acid optionally substituted, for example, by halogen, lower alkoxy or nitro, or of a carbonic acid semiester. Such acyl groups are, for example, lower alkanoyl, such as formyl, acetyl or propionyl, halo-lower alkanoyl, such as 2-haloacetyl, especially 2-fluoro-, 2-bromo-, 2-iodo-, 2,2,2-trifluoro- or 2,2,2-trichloro-acetyl, aroyl, such as optionally substituted benzoyl, for example benzoyl, halobenzoyl, such as 4-chlorobenzoyl, lower alkoxybenzoyl, such as 4-methoxybenzoyl, or nitrobenzoyl, such as 4-nitrobenzoyl. Also suitable is especially lower alkenyloxycarbonyl, for example allyloxycarbonyl, or lower alkoxycarbonyl optionally substituted in the 1- or 2-position, such as lower alkoxycarbonyl, for example methoxy- or ethoxy-carbonyl, optionally substituted benzyloxycarbonyl, for example benzyloxycarbonyl or 4-nitrobenzyloxycarbonyl, or aroylmethoxycarbonyl in which the aroyl group is benzoyl optionally substituted, for example, by halogen, such as bromine, for example phenacyloxycarbonyl or bromophenacyloxycarbonyl.

In a corresponding acylamino group acyl may represent especially alkanoylamino substituted by amino and/or by phenyl, carbamoyl, carboxy, imidazolyl, lower alkylthio, tetrahydropyrrolyl, hydroxy, indolyl or hydroxyphenyl, so that the term includes, for example, the acyl radicals of amino acids, for example naturally occurring amino acids, such as alanyl, asparaginyl, aspartyl, glycyl, histidyl, isoleucyl, leucyl, lysyl, methionyl, phenylalanyl, prolyl, seryl; threonyl, tryptophyl, tyrosyl or valyl; also included thereby are the acyl radicals of oligopeptides, for example di- or tri-peptides, such as oligopeptides of alanine, asparagine or aspartic acid.

In a diacylamino group diacyl is, for example, two acyl radicals as defined hereinbefore, or is, for example, the acyl radical of an organic dicarboxylic acid having, for example, up to 12 carbon atoms, especially a corresponding aromatic dicarboxylic acid, such as phthalic acid. Such a group is especially phthalimido. Esterified carboxy is, for example, carboxy esterified by an aliphatic or araliphatic alcohol, such as an unsubstituted or substituted lower alkanol or phenyl-lower alkanol, such as corresponding lower alkoxy- or phenyl-lower alkoxycarbonyl. Esterified carboxy is preferably pharmaceutically acceptable esterified carboxy, such as, for example, esterified carboxy that can be converted into carboxy under physiological conditions. These esters of formula I may also be called prodrug esters.

Carboxy esterified in a pharmaceutically acceptable manner is, for example, lower alkoxycarbonyl; lower alkoxycarbonyl substituted in a position higher than the $\alpha$-position by amino, by mono- or di-lower alkylamino or by hydroxy; lower alkoxycarbonyl substituted by carboxy, for example $\alpha$-carboxy-substituted lower alkoxycarbonyl; lower alkoxycarbonyl substituted by lower alkoxycarbonyl, for example $\alpha$-lower alkoxycarbonyl-substituted lower alkoxycarbonyl, aryl-lower alkoxycarbonyl, for example unsubstituted or substituted benzyloxycarbonyl, or pyridylmethoxycarbonyl;

lower alkanoyloxy-substituted methoxycarbonyl, for example pivaloyloxymethoxycarbonyl; lower alkoxymethoxycarbonyl substituted by lower alkanoyloxy or by lower alkoxy; bicyclo[2.2.1]heptyloxycarbonyl substituted methoxycarbonyl, such as bornyloxycarbonylmethoxycarbonyl; 3-phthalidoxycarbonyl; 3-phthalidoxycarbonyl substituted by lower alkyl, lower alkoxy or by halogen; or lower alkoxycarbonyloxy-lower alkoxycarbonyl, for example 1-(methoxy- or ethoxy-carbonyloxy)-ethoxycarbonyl.

Especially preferred prodrug esters are, for example, lower alkyl esters having up to four carbon atoms, such as, for example, butyl or ethyl esters, lower alkanoyloxymethyl esters, such as, for example, pivaloyloxymethyl ester, lower alkyl esters that have from two to four carbon atoms in each lower alkyl group and are substituted in a position higher than the α-position by di-lower alkylamino, such as, for example, 2-diethylaminoethyl ester, and also pyridylmethyl esters, such as 3-pyridylmethyl ester.

In amidated carboxy the amino group is, for example, amino that is unsubstituted, monosubstituted by hydroxy, or mono-or di-substituted by aliphatic radicals, such as amino, hydroxyamino, mono- or di-lower alkylamino or lower alkyleneamino having from 5 to 7 ring members. Preferably, amidated carboxy is pharmaceutically acceptable amidated carboxy, such as, for example, amidated carboxy that can be converted into carboxy under physiological conditions. Preferred pharmaceutically acceptable amides are compounds of formula I in which $R^6$ is carbamoyl, lower alkylcarbamoyl, for example ethylcarbamoyl, di-lower alkylcarbamoyl, for example diethylcarbamoyl, or in the form of N-(di-lower alkylamino)-lower alkylcarbamoyl, for example N-(2-diethylaminoethyl)carbamoyl or (3-diethylaminopropyl)carbamoyl.

Etherified hydroxy is, for example, hydroxy etherified by an aliphatic alcohol, such as hydroxy etherified by a lower alkanol, lower alkenol or lower alkynol each optionally substituted by halogen or, in a position higher than the α-position, by hydroxy, oxo, lower alkoxy, lower alkanoyloxy and/or mono- or di-lower alkylamino, and is, for example, lower alkoxy, halo-lower alkoxy, or corresponding hydroxy- oxo-, lower alkoxy-, lower alkanoyloxy- or mono- or di-lower alkylamino-lower alkoxy. Compounds in which $R^1$ and/or $R^2$ represent etherified hydroxy are esters of the phosphorus-containing acid group and, depending on the meaning of $R^2$, phosphonous acid esters, phosphinic acid esters or phosphonic acid esters. Preferred esters are the respective lower alkyl esters and hydroxy-lower alkyl esters.

Salts of compounds according to the invention are especially pharmaceutically acceptable non-toxic salts of compounds of formula I. Such salts are formed, for example, from the carboxy group present in compounds of formula I, and are especially metal or ammonium salts, such as alkali metal and alkaline earth metal salts, for example sodium, potassium, magnesium or calcium salts, and also ammonium salts with ammonia or suitable organic amines, such as lower alkylamines, for example methylamine, diethylamine or triethylamine, hydroxy-lower alkylamines, for example 2-hydroxyethylamine, bis-(2-hydroxyethyl)-amine, tris-(hydroxymethyl)-methylamine or tris-(2-hydroxyethyl)-amine, basic aliphatic esters of carboxylic acids, for example 4-aminobenzoic acid 2-diethylaminoethyl ester, lower alkylene-amines, for example 1-ethylpiperidine, lower alkylenediamines, for example ethylenediamine, cycloalkylamines, for example dicyclohexylamine, or benzylamines, for example N,N'-dibenzylethylenediamine, benzyltrimethylammonium hydroxide, dibenzylamine or N-benzyl-β-phenylethylamine. Compounds of formula I having a primary or secondary amino group may also form acid addition salts, for example with preferably pharmaceutically acceptable inorganic acids, such as hydrohalic acids, for example hydrochloric acid or hydrobromic acid, sulphuric acid, nitric acid or phosphoric acid, or with suitable organic carboxylic or sulphonic acids, for example acetic acid, propionic acid, succinic acid, glycolic acid, lactic acid, fumaric acid, maleic acid, tartaric acid, oxalic acid, citric acid, pyruvic acid, benzoic acid, mandelic acid, malic acid, ascorbic acid, pamoa acid, nicotinic acid, methanesulphonic acid, ethanesulphonic acid, hydroxyethanesulphonic acid, benzenesulphonic acid, 4-toluenesulphonic acid or naphthalenesulphonic acid.

It is also possible to use pharmaceutically unsuitable salts for isolation or purification. Only the pharmaceutically acceptable non-toxic salts are used therapeutically, and these are therefore preferred.

Aryl, also in definitions such as aroyl or aryl-lower alkoxycarbonyl, represents aromatic hydrocarbon radicals that are unsubstituted or substituted by lower alkyl, hydroxy, protected hydroxy, lower alkoxy, halogen, amino, halo-lower alkyl, hydroxy-lower alkyl, amino-lower alkyl or by nitro, and is, for example, unsubstituted or correspondingly substituted 1- or 2-naphthyl, but preferably unsubstituted or correspondingly substituted phenyl, such as phenyl, lower alkylphenyl, for example methylphenyl, hydroxyphenyl, halophenyl, for example 4-halophenyl, such as 4-chlorophenyl, benzyloxyphenyl, lower alkoxyphenyl, for example methoxyphenyl, hydroxymethylphenyl, aminomethylphenyl or nitrophenyl.

The general terms used hereinbefore and hereinafter, unless defined otherwise, have the following meanings:

The term "lower" indicates that groups or compounds so defined contain up to and including 8, preferably up to and including 4, carbon atoms.

Alkyl represents, for example, lower alkyl, such as methyl, ethyl, n-propyl, isopropyl, n-butyl, isobutyl or tert.-butyl, and also n-pentyl, n-hexyl, n-heptyl or n-octyl, preferably methyl, but may also represent, for example, nonyl, decyl, undecyl or dodecyl.

Arylalkyl represents, for example, aryl-lower alkyl in which aryl has the meanings given hereinbefore, and is especially, for example, unsubstituted phenyl-lower alkyl, such as benzyl or 1- or 2-phenylethyl.

Lower alkenyl contains preferably up to 6 carbon atoms and is bonded by way of an $sp^3$-hybridised carbon atom, and may be, for example, 2-propenyl, 2- or 3-butenyl or 3-pentenyl, but may also be vinyl.

Lower alkoxy represents especially methoxy, ethoxy, n-propoxy, isopropoxy, n-butoxy, isobutoxy or tert.-butoxy.

Halogen preferably has an atomic number of up to 35 and is especially chlorine, also fluorine or bromine, but may also be iodine.

Protected hydroxy is esterified hydroxy, for example hydroxy esterified as an acyl group, such as lower alkanoyloxy, benzyloxycarbohyloxy or lower alkoxycarbonyloxy, or etherified hydroxy, for example 2-tetrahydropyranyloxy or benzyloxy, and also lower alkoxy.

Halo-lower alkyl is, for example, halomethyl, such as fluoromethyl, trifluoromethyl or 1- or 2-chloroethyl.

Hydroxy-lower alkyl is, for example, mono- or di-hydroxy-lower alkyl, carries the hydroxy group(s), for example, especially in a position higher than the α-position and represents, for example, hydroxymethyl, 2-hydroxyethyl, 3-hydroxy- or 2,3-dihydroxy-propyl, 4-hydroxy- or 2,4-dihydroxy-butyl, or 5-hydroxy-, 2,5-dihydroxy- or 3,5-dihydroxy-pentyl.

Lower alkoxy-lower alkyl is, for example, mono- or di-lower alkoxy-lower alkyl, carries the lower alkoxy group(s), for example, especially in a position higher than the α-position and is, for example, 2-methoxy-, 2-ethoxy-, 2-propoxy- or 2-isopropoxy-ethyl, 3-methoxy- or 3-ethoxy-propyl or 3,3-dimethoxy-, 3,3-diethoxy, 2,3-dimethoxy- or 2,3-diethoxy-propyl or 4,4-dimethoxybutyl, and also methoxy-, ethoxy-, dimethoxy-, or propoxy- or isopropoxy-methyl.

Amino-lower alkyl is, for example, aminomethyl or 1- or 2-aminoethyl.

Lower alkanoyloxy is, for example, acetoxy, propionyloxy or butyryloxy, or also formyloxy or pivaloyloxy.

Lower alkoxycarbonyl is, for example, methoxycarbonyl or ethoxycarbonyl.

Aryl-lower alkoxycarbonyl is preferably phenyl-lower alkoxycarbonyl, for example, benzyloxycarbonyl or 1- or 2-phenylethoxycarbonyl.

Mono- or di-lower alkylamino is, for example methylamino, dimethylamino, ethylamino, diethylamino, propylamino, isopropylamino or butylamino.

The compounds prepared in accordance with the invention have valuable pharmacological properties. They are, for example, active and selective antagonists of N-methyl-D-aspartic acid (NMDA)-sensitive excitatory amino acid receptors in mammals. They are therefore suitable for the treatment of diseases that respond to a blocking of NMDA-sensitive receptors, such as, for example, cerebral ischaemia, muscular spasms (spasticity), convulsions (epilepsy), conditions of anxiety or manic conditions.

These advantageous effects may be demonstrated in in vitro or in in vivo test arrangements. For these, preferably mammals are used, for example mice, rats or monkeys, or tissue or enzyme preparations from such mammals. The compounds may be administered enterally or parentally, preferably orally; or subcutaneously, intravenously or intraperitoneally, for example in gelatin capsules or in the form of aqueous suspensions or solutions. The dosage to be used in vivo may range from 0.1 to 600 mg/kg, preferably from 1 to 300 mg/kg. In vitro, the compounds may be used in the form of aqueous solutions, the concentrations ranging from $10^{-4}$ to $10^{-9}$ molar solutions.

The inhibiting action on the NMDA-sensitive excitatory amino acid receptors may be determined in vitro by measuring, in accordance with G. Fagg and A. Matus, Proc. Nat. Acad. Sci., U.S.A., 81, 6876-80 (1984), to what extent the binding of L-$^3$H-glutamic acid to NMDA-sensitive receptors is inhibited. In vivo, the inhibiting action on NMDA-sensitive excitatory amino acid receptors may be demonstrated by the inhibition of NMDA-induced convulsions in mice.

The anti-convulsive properties of the compounds according to the invention may furthermore be shown by their effectiveness in preventing audiogenically induced attacks in DBA/2 mice (Chapman et al., Arzneimittel-Forsch. 34, 1261, 1984).

The anti-convulsive properties may furthermore be shown by the effectiveness of the compounds according to the invention as electric shock antagonists in mice or in rats.

An indication of the anxiolytic activity of the compounds of the present invention is given by their pronounced effectiveness in the conflict model according to Cook/Davidson (Psychopharmacologia 15, 159-168 (1968)).

The pronounced effectiveness of the compounds of formula I depends to a surprisingly high extent on the configuration at the double bond. For example, the racemate of D-2-amino-5-phosphono-3-cis-pentenoic acid known from Agric. Biol. Chem. 41, 573-579 (1979), B. K. Park et al., proves, for example in its ability to bond to the NMDA-sensitive receptor, to be far inferior to the racemate of the 2-amino-5-phosphono-3-trans-pentenoic acid according to the invention (in the Examples these compounds are referred to as compounds of the "E-series"). Compounds of the formula I, wherein the carbon atom carrying the group $R_6$ has R-configuration, have been found to be especially active.

Preferred are compounds of the formula I in which $R^3$ represents hydrogen, alkyl or aryl.

Also preferred are the compounds of the formula I in which $R^1$ represents hydroxy, lower alkoxy or hydroxy-lower alkoxy, $R^2$ represents hydrogen, alkyl, hydroxy, lower alkoxy or hydroxy-lower alkoxy, $R^3$ represents hydrogen, lower alkyl, halo-lower alkyl, hydroxy-lower alkyl, lower alkoxy-lower alkyl, phenyl-lower alkyl that is unsubstituted or substituted in the phenyl moiety, lower alkenyl, halogen, or unsubstituted or substituted phenyl, $R^4$ represents hydrogen, lower alkyl or unsubstituted or substituted phenyl, $R^5$ represents hydrogen or lower alkyl, $R^6$ represents carboxy or pharmaceutically acceptable esterified or amidated carboxy, $R^7$ represents amino, mono- or di-lower alkylamino, alkanoylamino or alkanoylamino substituted by halogen, by amino and/or by phenyl, carbamoyl, carboxy, imidazolyl, lower alkylthio, tetrahydropyrrolyl, hydroxy, indolyl or by hydroxyphenyl, benzoylamino or benzoylamino substituted by halogen, lower alkoxy or by nitro, or phthalimino, A represents unsubstituted or lower alkyl-substituted α,ω-alkylene having from 1 to 3 carbon atoms, or represents a bond, and B represents methylene or a bond, with the proviso that A is other than a bond when B represents a bond, wherein the substituents of phenyl are selected from the group consisting of lower alkyl, hydroxy, lower alkoxy, halogen, amino, halo-lower alkyl, hydroxy-lower alkyl, amino-lower alkyl and nitro, and pharmaceutically acceptable salts thereof.

Also preferred are compounds of the formula I in which $R^1$ to $R^5$ are as defined above, $R^6$ represents carboxy, alkoxycarbonyl, or alkoxycarbonyl substituted by amino, mono- or di-lower alkylamino, hydroxy or by lower alkanoyloxy, $R^7$ represents amino, mono-lower alkylamino, lower alkanoylamino or benzoylamino, and A and B are as defined above, and pharmaceutically acceptable salts thereof.

Likewise preferred are compounds of the formula I in which $R^1$, $R^2$, $R^5$ to $R^7$ and A and B are as defined immediately above and in which $R^3$ and $R^4$, independently of one another, each represents hydrogen, lower alkyl, phenyl, or phenyl substituted by lower alkyl, hydroxy, lower alkoxy, halogen, amino, halo-lower alkyl, hydroxy-lower alkyl, amino-lower alkyl or by nitro, and pharmaceutically acceptable salts thereof.

Especially preferred are compounds of the formula I in which $R^1$ represents hydroxy or lower alkoxy, $R^2$ represents hydrogen, alkyl, hydroxy or lower alkoxy, $R^3$ represents hydrogen, lower alkyl, phenyl, halophenyl, or phenyl-lower alkyl, $R^4$ and $R^5$ represent hydrogen or lower alkyl, $R^6$ represents carboxy, alkoxycarbonyl or hydroxy-lower alkoxycarbonyl, $R^7$ represents amino, mono-lower alkylamino, lower alkanoylamino or benzoylamino, A represents unsubstituted or lower alkyl-substituted $\alpha,\omega$-alkylene having from 1 to 3 carbon atoms or represents a bond and B represents methylene or a bond, with the proviso that A is other than a bond when B represents a bond, and pharmaceutically acceptable salts thereof.

Especially preferred are compounds of the formula I in which $R^1$ is hydroxy, $R^2$ represents hydrogen, alkyl or hydroxy, $R^3$ represents hydrogen, lower alkyl or halophenyl, $R^4$ represents hydrogen or halophenyl and $R^5$ represents hydrogen, $R^6$ represents carboxy, lower alkoxycarbonyl or hydroxy-lower alkoxycarbonyl, $R^7$ represents amino, mono-lower alkylamino, lower alkanoylamino or benzoylamino, A represents $\alpha,\omega$-alkylene having from 1 to 3 carbon atoms or represents a bond and B represents methylene or a bond, with the proviso that A is other than a bond when B represents a bond, and pharmaceutically acceptable salts thereof.

Most especially preferred are compounds of the formula I in which $R^1$ is hydroxy, $R^2$ represents hydrogen, lower alkyl or hydroxy, $R^3$ represents hydrogen or lower alkyl, $R^4$ and $R^5$ represent hydrogen, $R^6$ represents carboxy or lower alkoxycarbonyl, $R^7$ represents amino or mono-lower alkylamino, A represents $\alpha,\omega$-alkylene having from 1 to 3 carbon atoms, and B represents a bond, and pharmaceutically acceptable salts thereof.

Outstanding are the compounds of the formula I in which $R^1$ and $R^2$ represent hydroxy, $R^3$ represents hydrogen or lower alkyl, $R^4$ and $R^5$ represent hydrogen, $R^6$ represents carboxy, $R^7$ represents amino, A represents methylene and B represents a bond, and the carboxylic acid lower alkyl esters and pharmaceutically acceptable salts thereof, especially the R-enantiomers thereof with reference to the atom carrying the amino group.

The compounds of the present invention may be manufactured in a manner known per se, for example as follows:

a) in a compound of the formula II

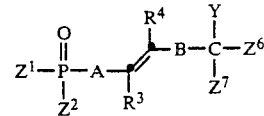

in which $Z^1$ has the meaning of $R^1$ or represents protected hydroxy, $Z^2$ has the meaning of $R^2$ or represents protected hydrogen or protected hydroxy, $R^3$, $R^4$, $R^5$, A and B are as defined for formula I, $Z^6$ has the meaning of $R^6$ or represents protected carboxy, $Z^7$ represents a protected group $R^7$ and $R^1$, $R^3$, $R^4$, $R^5$, A and B are as defined for formula I, the protected group $Z^7$ and when applicable, $Z^1$, $Z^2$ and/or $Z^6$ are freed, b) in order to obtain a compound of the formula I in which $R^5$ represents hydrogen, in a compound of the formula IV

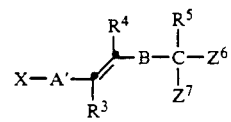

in which $R^3$, $R^4$, A and B are as defined for formula I, $Z^1$ has the meaning of $R^1$ or represents protected hydroxy, $Z^2$ has the meaning of $R^2$ or represents protected hydroxy or protected hydrogen, $Z^6$ has the meaning of $R^6$ or represents protected carboxy, $Z^7$ has the meaning of $R^7$ or represents protected amino, and Y represents an optionally esterified carboxy group that can be replaced by hydrogen, the group Y is replaced by hydrogen, or c) in order to obtain a compound of the formula I in which A represents unsubstituted or alkyl-substituted $\alpha,\omega$-alkylene having 2 or 3 carbon atoms and B represents methylene, a compound of the formula V

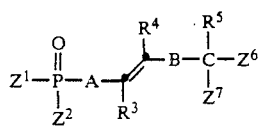

in which $R^3$, $R^4$, $R^5$ and B are as defined for formula I, $Z^6$ has the meaning of $R^6$ or represents protected carboxy, $Z^7$ has the meaning of $R^7$ or represents protected amino, X represents reactive esterified hydroxy and A' represents unsubstituted or alkylsubstituted $\alpha,\omega$-alkylene having 1 or 2 carbon atoms, is reacted with a compound of the formula VI

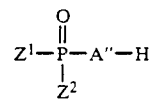

in which $Z^1$ has the meaning of $R^1$ or represents protected hydroxy, $Z^2$ has the meaning of $R^2$ or represents protected hydrogen or protected hydroxy and A" represents unsubstituted or alkyl-substituted methylene, which is present in metallated form, and any protected functional groups that may be present in a compound resulting from one of the preceding processes is freed and, if desired, a resulting compound of the formula I is converted into a different compound of the formula I and/or, if desired, a resulting compound of the formula I is converted into a salt or a resulting salt is converted into a different salt or into a free compound of the formula I and/or, if desired, an optical isomer is isolated from a mixture of stereoisomeric forms of a resulting compound of the formula I or of a salt thereof.

Protected hydroxy $Z^1$ and/or $Z^2$ in intermediates of formula II is, for example, hydroxy etherified by an aliphatic alcohol, such as hydroxy etherified by a lower alkanol, lower alkenol or lower alkynol each of which is unsubstituted or substituted by halogen or, in a position higher than the $\alpha$-position, by hydroxy, oxo, lower alkoxy, lower alkanoyloxy and/or by mono- or di-lower alkylamino, and is, for example, lower alkoxy, halo-lower alkoxy, or corresponding hydroxy-, oxo-, lower alkoxy-, lower alkanoyloxy- or mono- or di-lower alkylamino-lower alkoxy. Compounds of formula II in which $Z^1$ and/or $Z^2$ are etherified hydroxy are esters of the phosphorus-containing acid group and, depending on the meaning of $R^2$, are phosphonous acid esters, phosphinic acid esters or phosphonic acid esters. Preferred esters are the respective lower alkyl esters and hydroxy-lower alkyl esters.

Protected hydrogen $Z^1$ is protected in a manner known per se, such as is described, for example, in EP-A-0 009 348. Corresponding protecting groups are preferably groups of the formula —C($C_{1-4}$-alkyl)(OR$^a$)OR$^b$, preferably groups of the formula —CH(OR$^a$)OR$^b$ in which $R^{1a}$ and $R^b$ each represents $C_{1-4}$-alkyl. Especially suitable is the group —CH(OC$_2$H$_5$)$_2$.

Groups $Z^7$ in intermediates of formula II are, for example, $R^7$ groups substituted by acyl, that is to say acylamino that is unsubstituted or N-substituted by lower alkyl or by aryl-lower alkyl in which acyl is the acyl radical of an organic acid having, for example, up to 18 carbon atoms, especially an alkanecarboxylic acid that is unsubstituted or substituted, for example, by halo9en, amino or by phenyl, or benzoic acid that is unsubstituted or substituted, for example, by halogen, lower alkoxy or by nitro, or of a carbonic acid semiester. Such acyl groups are, for example, lower alkanoyl, such as formyl, acetyl or propionyl, halo-lower alkanoyl, such as 2-haloacetyl, especially 2-fluoro-, 2-bromo-, 2-iodo-, 2,2,2-trifluoro- or 2,2,2-trichloro-acetyl, aroyl, such as unsubstituted or substituted benzoyl, for example benzoyl, halobenzoyl, such as 4-chlorobenzoyl, lower alkoxybenzoyl, such as 4-methoxybenzoyl, or nitrobenzoyl, such as 4-nitrobenzoyl. The following are also especially suitable: lower alkenyloxycarbonyl, for example allyloxycarbonyl, or especially lower alkoxycarbonyl that is unsubstituted or substituted in the 1- or 2-position, such as, especially, lower alkoxycarbonyl, for example tertiary butoxycarbonyl and also methoxy- or ethoxy-carbonyl, and also unsubstituted or substituted benzyloxycarbonyl, for example benzyloxycarbonyl or 4-nitrobenzyloxycarbonyl, or aroylmethoxycarbonyl in which the aroyl group is benzoyl that is unsubstituted or substituted, for example, by halo9en, such as bromine, for example phenacyloxycarbonyl or bromophenacyloxycarbonyl.

Furthermore, in a corresponding acylamino group $Z^7$, acyl may be alkanoylamino substituted by amino and/or by phenyl, carbamoyl, carboxy, imidazolyl, lower alkylthio, tetrahydropyrrolyl, hydroxy, indolyl or by hydroxyphenyl, and thus includes, for example, the acyl radicals of amino acids, for example naturally occurring amino acids, such as alanyl, asparaginyl, aspartyl, glycyl, histidyl, isoleucyl, leucyl, lysyl, methionyl, phenylalanyl, prolyl, seryl, threonyl, tryptophyl, tyrosyl or valyl; also included are the acyl radicals of oligopeptides, for example di- or tri-peptides, such as oligopeptides of alanine, asparagine or aspartic acid.

Furthermore, protected amino $Z^7$ may be a diacylamino group. In this group diacyl is, for example, two acyl radicals of the definitions given hereinbefore, or diacyl is, for example, the acyl radical of an organic dicarboxylic acid having, for example, up to 12 carbon atoms, especially a corresponding aromatic dicarboxylic acid, such as phthalic acid. Such a group is especially phthalimido.

In addition, protected amino $Z^7$ may also be amino substituted by substituted lower alkoxycarbonyl, such as amino substituted by 2-halo-lower alkoxycarbonyl, for example 2,2,2-trichloroethoxycarbonyl, 2-chloroethoxycarbonyl, 2-bromoethoxycarbonyl or 2-iodoethoxycarbonyl, or by 2-(tris-substituted silyl)-ethoxycarbonyl, such as 2-tri-lower alkylsilylethoxycarbonyl, for example 2-trimethylsilylethoxycarbonyl or 2-(di-n-butyl-methyl-silyl)-ethoxycarbonyl, or by 2-triarylsilylethoxycarbonyl, such as 2-triphenylsilylethoxycarbonyl, or etherified mercaptoamino or silylamino, or may be in the form of an enamino, nitro or azido group.

An etherified mercaptoamino group is especially a phenylthioamino group that is unsubstituted or substituted by lower alkyl, such as methyl or tert.-butyl, lower alkoxy, such as methoxy, halogen, such as chlorine or bromine, and/or by nitro, or a pyridylthioamino group. Corresponding groups are, for example, 2- or 4-nitrophenylthioamino or 2-pyridylthioamino.

A silylamino group is especially an organic silylamino group. In such groups the silicon atom contains as substituent(s) preferably lower alkyl, for example methyl, ethyl, n-butyl or tert.-butyl, also aryl, for example phenyl. Suitable silyl groups are especially tri-lower alkylsilyl, especially trimethylsilyl or dimethyl-tert.-butylsilyl.

Enamino groups contain at the double bond in the 2-position an electron-attracting substituent, for example a carbonyl group. Protecting groups of this kind are, for example, 1-acyl-lower alk-1-en-2-yl radicals in which acyl is, for example, the corresponding radical of a lower alkane-carboxylic acid, for example acetic acid, of a benzoic acid that is unsubstituted or substituted, for example, by lower alkyl, such as methyl or tert.-butyl, lower alkoxy, such as methoxy, halogen, such as chlorine, and/or by nitro, or especially of a carbonic acid semiester, such as a carbonic acid lower alkyl semiester, for example methyl semiester or ethyl semiester, and lower alk-1-ene is especially 1-propene. Corresponding protecting groups are especially 1-lower alkanoyl-prop-1-en-2-yl, for example 1-acetylprop-1-en-2-yl, or 1-lower alkoxycarbonyl-prop-1-en-2-yl, for example 1-ethoxycarbonyl-prop-1-en-2-yl.

In the above-defined processes, protected hydroxy and protected amino have, for example, the meanings for protected hydroxy and for acyl-substituted amino given hereinbefore. Protected hydroxy represents especially lower alkoxy such as methoxy, ethoxy or isopropoxy, protected carboxy is especially tri-lower alkylsilyloxycarbonyl, such as trimethylsilyloxycarbonyl, and protected amino unsubstituted or substituted by lower alkyl or by aryl-lower alkyl is especially lower alkanoylamino, especially acetylamino or formylamino, N-lower alkanoyl-N-lower alkylamino, especially N-acetyl- or N-formyl-N-lower alkylamino, for example N-acetyl- or N-formyl-N-methylamino, or lower alkoxycarbonylamino, preferably tertiary butoxycarbonylamino. Another preferred exampled of protected hydroxy is trisubstituted silyl, such as tri-lower alkylsilyl, for example trimethylsilyl or tert.-butyldimethylsilyl.

Freeing the protected groups, that is to say setting free hydroxy $Z^1$ and/or $Z^2$, hydrogen $R^1$ from protected hydrogen $Z^1$, carboxy $R^6$ from protected carboxy $Z^6$ and/or optionally N-lower alylated or N-phenyl-lower alkylated amino $R^7$ from protected groups $Z^7$ can generally be effected either under hydrolytic conditions, such those of an acidic hydrolysis, for example in the presence of a hydrohalic acid, such as hydrochloric acid, preferably with heating, or by treatment with a tri-lower alkylhalosilane in an inert solvent, such as halogenated, preferably aliphatic hydrocarbon, for example dichloromethane or, less preferably, tri- or tetrachloromethane, trichloroethane or tetrachloroethane, in a temperature range of approximately from −25° to +50° C., preferably from approximately 0° C. to approximately 30° C., for example at temperatures in the region of room temperature, that is to say at from approximately 15° C. to approximately 25° C., advantageously under substantially anhydrous conditions and under an inert gas, for example under argon or nitrogen.

In process a), if several of the groups $Z^1$, $Z^2$, $Z^6$ and $Z^7$ represent protected groups, the reaction conditions can be so selected that they can be freed in single step, or that, for example, esterified carboxy $Z^6$ is retained.

Thus, if compounds of the formula I in which $R^6$ denotes carboxy, are desired as end products, compounds of formula II, wherein $Z^6$ is esterified or amidated carboxy, for example lower alkoxycarbonyl, can be used as starting materials. When hydrolytic conditions are applied or on treatment with a tri-lower alkyljodosilane, the carboxy group $R^6$ is set free under the condition of the cleavage of the protected groups $Z^1$, $Z^2$ and $Z^7$.

Alternatively, if compounds of formula I in which $R^6$ is esterified or amidated carboxy, such as lower alkoxycarbonyl or carbamoyl, are desired as end products, the starting materials of formula II and the process conditions can be so selected that although in the last step $Z^1$, $Z^2$ and $Z^7$ are freed, $Z^6$, which represents the desired $R^6$ group, remains uneffected.

An especially preferred process variant is accordingly directed to the manufacture of compounds of formula I in which $R^6$ is lower alkoxycarbonyl and $R^7$ is amino. In this process variant the starting materials used are preferably compounds of formula II in which $Z^1$ and $Z^2$ are lower alkoxy or lower alkoxy substituted in a position higher than the α-position by halogen, such as chlorine, $Z^6$ is lower alkoxycarbonyl and $Z^7$ is lower alkanoylamino, such as formylamino, or lower alkoxycarbonylamino, such as tert.-butoxycarbonylamino. Starting from such compounds of formula II the freeing of the protected groups can be so controlled by treatment in an inert solvent, such as a halogenated hydrocarbon, for example dichloromethane, at temperatures in the region of room temperature, with a reagent such as trimethylbromosilane, and by subsequent treatment with a lower alkanol, such as ethanol, and a substance absorbing hydrogen halide, such as an aliphatic epoxide, especially an epoxy-lower alkane, for example propylene oxide, that compounds of formula I in which $R^2$ is hydroxy, $R^6$ is $C_1$-$C_4$alkoxycarbonyl, $R^7$ is amino and the variables $R^3$, $R^4$ and $R^5$ are as defined for formula I, are obtained directly.

This process is especially preferred for the manufacture of compounds of formula I in which A is methylene or 1,3-propylene and B is a bond, $R^4$ and $R^5$ are hydrogen and $R^3$ is alkyl having up to 4 carbon atoms, such as methyl.

Another especially preferred process variant is the manufacture of compounds of formula I in which $R^6$ is carboxy. In this case the starting materials used are preferably compounds of formula II in which $Z^1$ and $Z^2$ are lower alkoxy or lower alkoxy substituted in a position higher than the α-position by halogen, such as chlorine, $Z^6$ is optionally protected carboxy and $Z^7$ is lower alkoxycarbonylamino, especially α-branched lower alkoxycarbonylamino, such as tert.-butoxycarbonylamino. In this case, the carboxy group is preferably, but not necessarily, intermediately protected, for example by treatment with a silylation agent, such as an N,O-silyl-lower alkanoic acid amide, for example with N,O-trimethylsilylacetamide.

Working up is carried out in a manner known per se, two purifying methods especially having proved advantageous. Either the crude product can be converted into a readily volatile derivative, for example by silylation, and recovered as such by distillation and then desilylated, or the crude product can be treated with an agent that reacts with excess acid, such as hydrohalic acid, thereby removing it. Suitable agents are, for example, compounds to which a corresponding acid can be added, for example lower alkylene oxides (epoxides), such as propylene oxide.

Intermediates of formula II are preferably manufactured by reacting a compound of formula

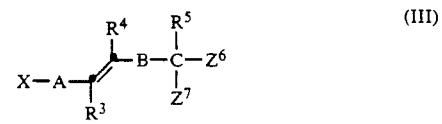
(III)

in which $R^3$, $R^4$, $R^5$, A and B are as defined for formula I, $Z^6$ has the meaning of $R^6$ or is protected carboxy, $Z^7$ is a protected $R^7$ group and X is reactive esterified hydroxy, with a compound of formula

(IV)

in which $Z^1$ is free or protected hydroxy, $Z_2$ has the meaning of $R_1$ or is protected hydroxy and R is an etherifying group, and can be used without being isolated or specially purified. According to another preferred process variant, a compound of formula

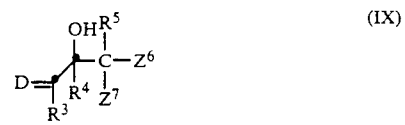
(IX)

is subjected to selective halogenation, for example by means of thionyl chloride, to form the corresponding intermediate III, and this is reacted in situ, that is to say without being isolated, with component IV.

The etherifying group R is, for example, phenyl-lower alkyl, trisubstituted silyl, such as tri-lower alkylsilyl or, preferably, alkyl. The reaction is carried out in a manner known per se, especially under the known conditions of the Michaelis-Arbuzov reaction.

According to one variant of this process the reaction, for example, of a trialkyl phosphite of the formula IV, such as triethyl phosphite, especially with compounds of the formula III in which A represents a bond, can be catalysed in a suitable manner, such as by a halide of a metal of sub-group VIII, preferably a nickel, palladium or platinum halide, especially nickel chloride.

It is preferable to carry out this process with compounds of the formulae III and IV in which $R^3$, $R^4$, $R^5$, A and B are as defined for formula I, $Z^1$ represents protected hydroxy, $Z^2$ represents lower alkyl, protected hydrogen or protected hydroxy, R represents lower alkyl, $Z^6$ represents free protected or esterified carboxy, $Z^7$ represents a protected group $R^7$ and X represents reactive esterified hydroxy and, following the reaction in which the compound RX becomes free, to free the protected groups $Z^1$, $Z^2$, $Z^7$ and, if applicable and/or desired $Z^6$. In this case preferably $Z^1$ represents lower alkoxy, $Z^2$ represents lower alkyl, di-lower alkoxy-lower alkyl or lower alkoxy, R represents lower alkyl, $Z^6$ represents carboxy or lower alkoxycarbonyl, $Z^7$ represents optionally N-lower alkylated or N-phenyl-lower alkylated formylamino or tert.butoxycarbonyl and X represents halogen.

Compounds of formula III can be manufactured, for example, by reacting an N-protected aminomalonic acid ester of formula V

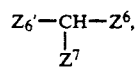

(V)

in which $Z^6$ and $Z_6'$ are identical or different esterified carboxy groups, for example lower alkoxycarbonyl groups, in a manner known per se with a compound of formula

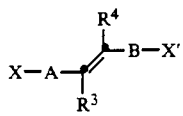

(VI)

in which X and X′, independently of one another, each represents reactive esterified hydroxy, such as halogen. The resulting compounds of formula

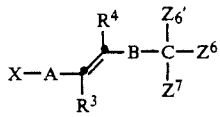

(VII)

can be converted into compounds of formula III in which $R^5$ is hydrogen by hydrolysis, for example under hydrolytic conditions, such as the conditions of an acidic hydrolysis, for example with hydrohalic acids, such as hydrochloric acid, preferably with heating, and by decarboxylation, or by dealkoxycarbonylation, without previous hydrolysis, by heating in an aqueous aprotic solvent, such as dimethyl sulphoxide, in the presence of an alkali metal halide, such as sodium chloride.

This variant is accordingly especially suitable for producing compounds III in which $R^5$ is hydrogen, $Z^6$ is free or esterified carboxy and $Z^7$ is protected amino, such as lower alkanoylamino.

Intermediates III in which A is methylene that is unsubstituted or substituted by alkyl, B is a bond, X is halogen and $Z^7$ is formylamino can furthermore be produced by reacting a compound of formula

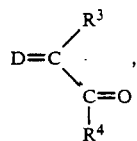

(VIII)

wherein D denotes optionally alkylated methylidene, such as a corresponding α,β-unsaturated aldehyde, for example acrolein in or methacrolein, with an α-isocyanoacetic acid derivative, such as an α-isocyanoacetic acid lower alkyl ester. With suitable catalysis, such as with low valency metal salts, that is to say metal salts derived from metals of groups I and II of the Periodic Table of Elements, for example corresponding metal oxides or metal halides, such as zinc chloride, cadmium chloride, silver oxide or, preferably, copper oxide or complexes of gold-I-tetrafluoroborate with aliphatic or cycloaliphatic isocyanides, for example bis(cyclohexylisocyanide)gold-I-tetrafluoroborate, there are thus obtained in a manner known per se 5-vinyl-2-oxazoline-4-carboxylic acid derivatives, for example esters of formula

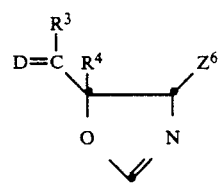

(IX)

which can be converted into the open-chained compounds of formula

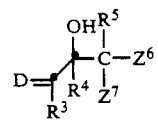

(X)

in which D is unsubstituted or alkyl-substituted methylidene. These compounds can in turn be converted by selective halogenation, such as bromination or chlorination, preferably with cooling and with displacement of the double bond in the manner of an allyl rearrangement, into compounds of formula III.

Another process for the manufacture of compounds II in which $R^5$ is hydrogen, A is methylene or 1,3-propylene and $R^6$ is carboxy, is based on the principle that a compound of formula

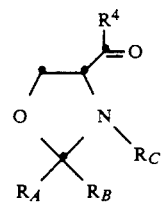

(XI)

in which $R_A$ and $R_B$ are hydrogen or preferably lower alkyl, such as methyl, and $R_C$ is an amino-protecting group, is condensed with a 2-$R^3$-acetic acid ester or condensed first with a 1-$R^3$-ethene-metal compound, for example with isopropenylmagnesium bromide, and subsequently with an acetic acid ester, in the resulting compound of formula

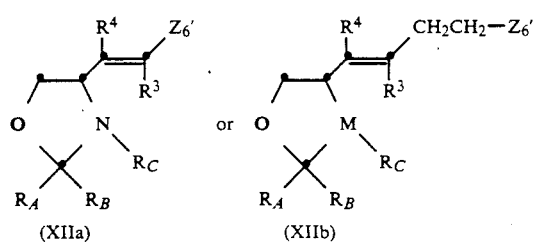

(XIIa)    (XIIb)

in which $Z_6'$ is esterified carboxy, for example lower alkoxycarbonyl, this group is reduced to hydroxymethyl, for example by means of diisobutylaluminium hydride, the hydroxymethyl group is halogenated, for example brominated by means of tetrabromomethane-/triphenylphosphine, the resulting compound of formula

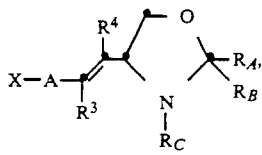
(XIII)

in which A denotes methylene or 1,3-propylene and X is halogen, for example bromine, is further reacted with a compound of formula IV, the oxazolidine ring is cleaved, for example, by means of an ion exchanger, such as Amberlyst 15 ®, and, in the resulting compound of formula

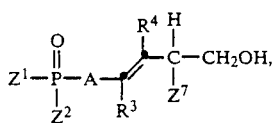
(XIV)

in which $Z^7$ is a protected amino group of formula $R_C$—NH—(II'), the hydroxymethyl group is oxidised to carboxy in customary manner.

When carrying out the above-described processes for the manufacture of intermediates III and the further reaction of the same to form intermediates II it is not necessary to isolate all of the intermediate stages. For example, especially the conversion of compounds X into compounds III and the further reaction thereof with compounds IV to form intermediates II can advantageously be carried out in situ.

Attention is drawn in this connection to the surprising finding that the manufacture of the intermediates II and their further reaction according to the invention to form the end products I can be carried out stereoselectively. That is, neither in the reaction sequence III+IV→II or IIa→I, nor in the reaction sequences X→III and XI→XII→XIII→XIV→II is there reversal of configuration or significant racemisation. The process of the invention is therefore excellently suitable for the direct manufacture of compounds of formula I with the preferred R-configuration at the carbon atom carrying the amino group $R^7$. The invention also relates to the manufacture of sterically homogeneous compounds of formula I and sterically homogeneous intermediates of formulae II, III, X, XI, XII, XIII and/or XIV.

According to another preferred process variant, a compound of formula

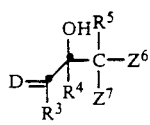
(X)

is subjected to selective halogenation, for example by means of thionyl chloride, to form the corresponding intermediate III, and this is reacted in situ, that is to say without being isolated, with component IV.

In process b), the group Y represents carboxy or esterified carboxy as defined hereinbefore, especially lower alkoxycarbonyl. Replacement of the group Y by hydrogen can be carried out, for example, under conditions under which first esterified carboxy is hydrolysed and then carboxy is replaced by hydrogen (decarboxylation), such as under hydrolytic conditions, such as those of an acidic hydrolysis, for example with hydrohalic acid, such as with hydrochloric acid, preferably while heating. In this process, if several of the groups $Z^1$, $Z^2$, $Z^6$ and $Z^7$ represent protected groups, these may advantageously be so selected that they can be freed together in the step in which the hydrolysis and the decarboxylation is effected.

The replacement of the group Y by hydrogen can also be carried out without previous hydrolysis, as a dealkoxycarbonylation, for example according to A. P. Krapcho, Tetrahedron Letters 957 (1973), such as by heating in an aqueous aprotic solvent, such as dimethyl sulphoxide, in the presence of an alkali halide, such as sodium chloride.

It is preferable to carry out this process with compounds of the formula IV in which $R^3$, $R^4$, A and B are as defined for formula I, $Z^1$ represents protected hydroxy, $Z^2$ represents lower alkyl, protected hydrogen or protected hydroxy, $Z^6$ represents protected carboxy, $Z^7$ represents protected amino and Y represents an optionally esterified carboxy group that can be replaced by hydrogen, and for the protected groups to be freed together in the step in which the group Y is replaced by hydrogen. In this case preferably $Z^1$ represents lower alkoxy, $Z^2$ represents lower alkyl, di-lower alkoxy-lower alkyl or lower alkoxy, $Z^6$ and Y represent lower alkoxycarbonyl and $Z^7$ represents lower alkanoylamino.

The compounds of the formula IV may be manufactured, for example, analogously to process a) by reacting a compound of the formula II'

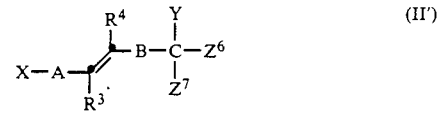
(II')

with a compound of the formula III

(III)

in which all radicals have the meanings given hereinbefore. The compounds of the formula II' may in turn be manufactured from a compound of the formula VII and an N-protected aminomalonic acid ester, as described in process a).

In process c), the group —A"—H is an alkyl group which may be metallated in the α-position to phosphorus by a suitable base, such as an organoalkali metal compound, for example butyllithium. A correspondingly metallated compound of the formula VI is then alkylated with a compound of the formula V in a manner known per se.

The manufacture of compounds of the formula V can be carried out analogously to the manufacture of compounds of the formula II. The compounds of the formula VI are alkylphosphonic acid dialkyl esters ($Z^1$ and $Z^2$=alkoxy) or phosphinic acid esters ($Z^1$=alkoxy, $Z^2$=alkyl). These compounds are known or may be manufactured in a manner known per se.

To convert a resulting compound of the formula I into a different compound of the formula I conversions such as the following may be carried out:

As mentioned, compounds obtainable in accordance with the invention can be converted into different compounds of formula I. In particular, a free amino group $R^7$ may be substituted, for example converted into an unsubstituted or phenylated alkylamino group, free carboxy $R^6$ may be esterified, or esterified or amidated carboxy $R^6$ may be converted into free carboxy, and/or free or esterified carboxy $R^6$ may be converted into amidated carboxy.

To convert an amino group into an unsubstituted or phenylated alkylamino group the amino group may be alkylated by substitution, for example with a reactive esterified optionally phenylated alkanol, such as an alkyl halide, or by reduction, such as with an aldehyde or ketone, and also with catalytically activated hydrogen or, in the case of formaldehyde, advantageously with formic acid as reducing agent.

Compounds of the formula I in which $R^7$ represents amino may be converted into compounds in which $R^7$ represents acylamino, for example using a corresponding acid anhydride or halide, or vice versa, by processes belonging to the State of the Art and described herein in connection with protecting groups.

Free carboxylic acids of formula I or salts thereof may be converted according to known processes by suitable alcohols or corresponding derivatives thereof into the corresponding esters, that is to say into compounds of formula I that are, for example, in the form of lower alkyl esters, aryl-lower alkyl esters, lower alkanoyloxymethyl esters or lower alkoxycarbonyl-lower alkyl esters.

For the esterification, a carboxylic acid may be reacted directly with a diazoalkane, especially diazomethane, or with a corresponding alcohol in the presence of a strongly acidic catalyst (for example a hydrohalic acid, sulphuric acid or an organic sulphonic acid) and/or of a dehydrating agent (for example dicyclohexylcarbodiimide). Alternatively, the carboxylic acid may be converted into a reactive derivative, such as into a reactive ester, or into a mixed anhydride, for example with an acid halide (for example, especially an acid chloride), and this activated intermediate is reacted with the desired alcohol.

Compounds of formula I in which $R^6$ is esterified carboxy, such as, especially, lower alkoxycarbonyl, for example ethoxycarbonyl, can be converted into compounds of formula I in which $R^6$ is carboxy, for example by hydrolysis especially in the presence of inorganic acids, such as hydrohalic acids or sulphuric acid or, less preferably, aqueous alkalis, such as alkali metal hydroxides, for example lithium or sodium hydroxide. In this connection attention is drawn to the fact that also carboxy can be freed from esterified carboxy in such a manner that no significant racemisation occurs. This can be achieved especially by treatment with from approximately 0.2N to approximately 4N, for example approximately 1N, that is to say from approximately 0.5N to approximately 2N, aqueous mineral acid, if necessary while heating, for example at from approximately 60° C. to approximately boiling temperature, that is to say approximately 100° C. Surprisingly, the hydrolysis, for example, of phosphonic acid carboxylic acid lower alkyl esters of formula I, proceeds with a high yield even without the addition of acidic or basic reagents. A preferred process for the manufacture of carboxylic acids of formula I from the corresponding lower alkyl esters, such as the respective ethyl esters, therefore consists in acidic hydrolysis by treatment with from approximately 0.2N to approximately 4N aqueous mineral acid, for example hydrochloric acid, sulphuric acid, phosphoric acid or the like, and also in the—possibly autocatalytic—hydrolysis in water, preferably at elevated temperatures, such as with heating under reflux.

The above reactions are carried out according to standard methods in the absence or presence of diluents, preferably those that are inert towards the reagents and are solvents therefor, in the presence of catalysts, condensation agents or the other agents and/or in an inert atmosphere, at low temperature, room temperature or elevated temperature, preferably at the boiling point of the solvents used, at atmospheric or superatmospheric pressure.

The invention includes furthermore any variant of the present processes in which an intermediate obtainable at any stage of that process is used as starting material and the remaining steps are carried out, or the process is discontinued at any stage, or in which the starting materials are formed under the reaction conditions or in which the reactants are used in the form of their salts or optically pure antipodes. There should especially be used in these reactions those starting materials that result in the formation of the compounds mentioned hereinbefore as being especially valuable.

The invention relates also to novel starting materials and processes for their manufacture.

Depending on the choice of starting materials and methods, the novel compounds may be in the form of one of the possible optical isomers or in the form of mixtures thereof, for example depending on the number of asymmetric carbon atoms they may be in the form of pure optical isomers, such as antipodes, or mixtures of optical isomers, such as racemates, or mixtures of diastereoisomers from which one antipode, if desired, may be isolated.

Resulting mixtures of diastereoisomers and mixtures of racemates may be separated in known manner on the basis of the physico-chemical differences between the constituents into the pure isomers, diastereoisomers or racemates, for example by chromatography and/or fractional crystallisation.

The resulting racemates (racemic diastereoisomers) may furthermore be separated into the optical antipodes according to methods known per se, for example by recrystallisation from an optically active solvent, with the aid of microorganisms or enzyme-catalyst in free or in an immobilised form or by reaction of an acidic end product with an optically active base that forms salts with the racemic acid, and separation of the salts obtained in this manner, for example on the basis of their different solubilities, into the diastereoisomers, from which the antipodes can be freed by the action of suitable agents. Basic racemic products can also be separated into the antipodes, for example by separation of the diastereoisomeric salts thereof, for example by fractional crystallisation of the d- or l-tartrates thereof. Any racemic intermediate or starting material can be separated in a similar manner.

Finally, the compounds according to the invention are obtained either in free form or in the form of their salts. Any resulting base can be converted into a corresponding acid addition salt, preferably using a pharmaceutically acceptable acid or an anion-exchange preparation, or resulting salts can be converted into the corresponding free bases, for example using a stronger base, such as a metal or ammonium hydroxide or a basic salt, for example an alkali metal hydroxide or carbonate, or a cation-exchange preparation. A compound of formula I can also be converted into the corresponding metal or ammonium salts. These or other salts, for example the picrates, can also be used for the purification of resulting bases. The bases are converted into salts, the salts are separated and the bases are freed from the salts. In view of the close relationship between the free compounds and the compounds in the form of their salts, whenever a compound is mentioned in this Application, a corresponding salt of that compound is also included, provided that this is possible or appropriate under the given circumstances.

The compounds, including their salts, can also be obtained in the form of their hydrates or contain other solvents used for the crystallisation.

The pharmaceutical preparations according to the invention are those that are suitable for enteral, such as oral or rectal, and parenteral administration to mammals, including man, for the treatment or prevention of diseases that respond to the blocking of NMDA-receptors, such as, for example, cerebral ischaemia, muscular spasms (spasticity), convulsions (epilepsy), conditions of anxiety or manic conditions. They comprise an effective amount of a pharmacologically active compound of formula I or a pharmaceutically acceptable salt thereof, on its own or in combination with one or more pharmaceutically acceptable carriers.

The pharmacologically active compounds of the invention can be used in the manufacture of pharmaceutical compositions that comprise an effective amount of the active compound on its own or in conjunction or admixture with excipients or carriers that are suitable for enteral or parenteral administration. Preferred are tablets and gelatin capsules that comprise the active constituent together with a) diluents, for example lactose, dextrose, sucrose, mannitol, sorbitol, cellulose and/or glycine, b) glidants, for example silicon dioxide, talc, stearic acid, the magnesium or calcium salt thereof and/or polyethylene glycol, for tablets also c) binders, for example magnesium aluminium silicate, starch paste, gelatin, tragacanth, methylcellulose, sodium carboxymethylcellulose and/or polyvinylpyrrolidone, if desired d) dispersing agents or disintegrators, for example starches, agar, alginic acid or the sodium salt thereof, or foaming mixtures and/or e) absorbents, colouring agents, flavourings and sweeteners. Injectable preparations are preferably aqueous isotonic solutions or suspensions, and suppositories are advantageously produced from fatty emulsions or suspensions. These compositions may be sterilised and/or contain adjuvants, such as preservatives, stabilisers, wetting agents or emulsifiers, solubilisers, salts for regulating the osmotic pressure and/or buffers. In addition they may also contain other therapeutically valuable substances. These preparations are manufactured according to conventional mixing, granulating or coating methods and contain approximately from 0.1 to 100%, preferably approximately from 1 to 50%, active constituent. A unit dose for a mammal weighing approximately from 50 to 70 kg may contain approximately from 1 to 500 mg, preferably approximately from 10 to 500 mg, of active constituent.

The following Examples are intended to illustrate the invention and do not represent limitations. The temperatures are in degrees Celsius and all parts are quoted in the form of parts by weight. Unless stated otherwise, all evaporation is carried out under reduced pressure, preferably approximately from 2 to 13 Kilopascal (kPa).

EXAMPLE 1

8.22 g of E-2-formylamino-5-diethylphosphono-3-pentenoic acid ethyl ester are dissolved in 170 ml of 6N hydrochloric acid and the whole is heated under reflux for 22 hours. After concentration in vacuo, the oily residue is taken up in a small amount of ethanol and the mixture is again concentrated by evaporation in vacuo. This procedure is repeated a further twice. The resulting residue is dissolved in 15 ml of ethanol and 20 ml of ethanol/propylene oxide (1:1) are added dropwise. The resulting brownish-coloured precipitate is filtered off and purified by ion exchange chromatography (Dowex $50W \times 8/H_2O$). After concentration and lyophilisation, E-2-amino-5-phosphono-3-pentenoic acid is obtained in the form of a white amorphous powder, $^1$H-NMR ($D_2O$): 2.39 (dd, 2H, C(5)—H); 4.27 (d, 1H, C(2)—H); 5.53 (m, 1H, C(3)—H); 5.87 (m, 1H, C(4)—H), m.p. after recrystallisation from ethanol/water 191°-192°.

The starting material is manufactured as follows:

1.6 g of red copper(I) oxide are added to 200 ml of benzene. With intensive stirring, a solution of 140 g of isocyanoacetic acid ethyl ester and 84 g of freshly distilled acrolein in 200 ml of benzene are added dropwise to this suspension within a period of 10 minutes. During the course of this addition the reaction temperature is maintained between 30° and 32° by cooling with ice. When the addition is complete the mixture is maintained at 30°-32° until the exothermic reaction has subsided, and then the whole is stirred for 1 hour at room temperature. After excess copper(I) oxide has been removed by filtration, the filtrate is concentrated by evaporation in vacuo at 30°. 600 ml of ether are added to the residue, and the whole is filtered over celite and concentrated to dryness by evaporation in vacuo. In this manner 5-vinyl-2-oxazoline-4-carboxylic acid ethyl ester is obtained in the form of a pale yellow oil, b.p. 100°-110° (5.3 Pa).

128 g of the 5-vinyl-2-oxazoline-4-carboxylic acid ethyl ester are dissolved in 70 ml of tetrahydrofuran, and 27.4 g of water and 3.5 g of triethylamine are added. The reaction mixture is stirred for 62 hours at 65°-70° and, having been cooled, is taken up in 200 ml of dichloromethane. The solution is dried over 200 g of magnesium sulphate, filtered and concentrated by evaporation in vacuo. Purification by column chromatography (silica gel;hexane/ethyl acetate 3:2) of the viscous oil that remains yields 2-formylamino-3-hydroxy-4-pentenoic acid ethyl ester in the form of a diastereoisomeric mixture, m.p. 50°-51°.

2.0 g of 2-formylamino-3-hydroxy-4-pentenoic acid ethyl ester in 80 ml of dry tetrahydrofuran are cooled to $-78°$. 2.5 ml of thionyl bromide are slowly added dropwise thereto in such a manner that the reaction temperature does not exceed $-75°$. When the addition is complete, the reaction solution is warmed within a period of approximately 3 hours to 0° and is stirred at that temperature for 2.5 hours. The orange-yellow solution is then poured onto 300 ml of a cold (5°-10°) saturated aqueous sodium hydrogen carbonate solution and extracted with dichloromethane. The organic extracts are dried over magnesium sulphate and concentrated by evaporation in vacuo at room temperature. The oil that remains is dissolved in 20 ml of triethyl phosphite and heated for 2 hours in vacuo (10 kPa) under reflux (55°). Excess triethyl phosphite is then distilled off under a high vacuum. Purification by column chromatography (silica gel, ethyl acetate/hexane (2:1), then ethyl acetate) yields E-2-formylamino-5-diethylphosphono-3-pentenoic acid ethyl ester in the form of a pale yellow oil; $^1$H-NMR(CDCl$_3$): 2.62 (m, 2H, C(5)—H); 5.19 (m, 1H, C(2)—H); 5.75 (m, 2H, C(3)—H and C(4)—H).

EXAMPLE 2

E-2-amino-4-methyl-5-phosphono-3-pentenoic acid is obtained by hydrolysis of E-2-formylamino-4-methyl-5-diethylphosphono-3-pentenoic acid ethyl ester in a manner analogous to that described in Example 1, $^1$H-NMR (D$_2$O): 1.73 (s, 3H, CH$_3$); 4.55 (s, 1H,C(2)—H).

The starting material is manufactured as follows:

By reaction of isocyanoacetic acid ethyl ester with methacrolein in a manner analogous to that described in Example 1, and after subsequent fractional distillation, 5-(2-propenyl)-2-oxazoline-4-carboxylic acid ethyl ester is obtained in the form of a colourless oil, b.p. 110°-130° (5.3 Pa).

2-Formylamino-3-hydroxy-4-methyl-4-pentenoic acid ethyl ester, m.p. 67°, is obtained by hydrolysis of 5-(2-propenyl)-2-oxazoline-4-carboxylic acid ethyl ester in a manner analogous to that described in Example 1.

By reaction of 2-formylamino-3-hydroxy-4-methyl-4-pentenoic acid ethyl ester with thionyl bromide and subsequent treatment with triethyl phosphite in a manner analogous to that described in Example 1, E-2-formylamino-4-methyl-5-diethylphosphono-3-pentenoic acid ethyl ester is obtained in the form of a pale yellow oil.

EXAMPLE 3

By hydrolysis of E-2-formylamino-5-(O-ethylmethylphosphonyl)-3-pentenoic acid ethyl ester in a manner analogous to that described in Example 1, after precipitation with propylene oxide E-2-amino-5-methylphosphonyl-3-pentenoic acid is obtained in the form of an amorphous white powder, $^1$H-NMR (D$_2$O): 2.55 (dd, 2H, C(5)—H); 4.38 (d, 1H, C(2)—H); 5.64 (m, 1H, C(3)—H); 5.91 (m, 1H, C(4)—H).

The starting material is manufactured as follows:

By reaction of E-2-formylamino-3-hydroxy-4-pentenoic acid ethyl ester with thionyl bromide and subsequent treatment with methylphosphonous acid diethyl ester instead of triethyl phosphite in a manner analogous to that described in Example 1, E-2-formylamino-5-(O-ethyl-methylphosphonyl)-3-pentenoic acid ethyl ester is obtained in the form of a colourless oil, $^1$H-NMR (CDCl$_3$): 2.63 (dd, 2H, C(5)—H); 5.1 (m, 1H, C(2)—H); 5.75 (m, 2H, C(3)—H) and C(4)—H).

EXAMPLE 4

25 g of E-2-formylamino-5-O-ethyl-diethoxymethylphosphonyl-3-pentenoic acid ethyl ester are stirred under reflux for 16 hours with 500 ml of 6N hydrochloric acid and the whole is then concentrated in vacuo at 70°. The residue is suspended in 100 ml of 95% ethanol/water, 20 ml of propylene oxide are added and the product is filtered off. Recrystallisation from water yields E-2-amino-5-phosphino-3-pentenoic acid, m.p. 139°-140°.

The starting material is manufactured as follows:

10 g of 2-formylamino-3-hydroxy-4-pentenoic acid ethyl ester in 50 ml of dry tetrahydrofuran are cooled to −78°. 12.7 g of thionyl chloride are added dropwise in such a manner that the reaction temperature does not exceed −75°. Subsequently, the reaction solution is warmed to −20° within a period of 3 hours and stirred at that temperature for 3 hours. The yellow solution is then poured onto 300 ml of a cold (5°) saturated aqueous sodium hydrogen carbonate solution and extracted with dichloromethane. The organic extracts are dried over sodium sulphate and concentrated by evaporation in vacuo at 30°. The residue is pre-purified by column chromatography (silica gel, ethyl acetate), and the light-yellow oil that remains is dissolved in 10 ml of tetrahydrofuran. After the addition of 17.0 g of diethoxymethylphosphonous acid ethyl trimethylsilyl ester, the whole is stirred for 24 hours at 35°. The dark-yellow solution is then poured onto 100 ml of a cold (5°) saturated sodium hydrogen carbonate solution and extracted with dichloromethane. The organic extracts are dried over sodium sulphate and concentrated by evaporation in vacuo at 30°. After purification of the residue by column chromatography (silica gel, ethyl acetate/methanol), E-2-formylamino-5-O-ethyl-diethoxymethylphosphonyl-3-pentenoic acid ethyl ester is obtained in the form of a light-yellow oil, $^1$H-NMR (CDCl$_3$): 2.70 (m, 2H, C(5)—H); 4.68 (q, 1H, C(2)—H); 5.20 (m, 1H, (C—P)—H); 5.80 (m, 2H, C(3)—H and C(4)—H).

EXAMPLE 5 a) 1.0 g of E-2-amino-5-phosphino-3-pentenoic acid is suspended in 20 ml of ethanol and the suspension is saturated with hydrogen chloride gas for 2 hours at 65°. After concentration, the residue is dissolved in 10 ml of ethanol, 10 ml of propylene oxide are added and the precipitate is filtered off. Recrystallisation from water/acetone 1:1 yields E-2-amino-5-phosphino-3-pentenoic acid ethyl ester, m.p. 172°-173°.

b) 1.0 g of E-2-amino-5-phosphino-3-pentenoic acid is suspended in 20 ml of n-butanol and the suspension is saturated with hydrogen chloride gas for 3 hours at 60°. After concentration, the residue is dissolved in 15 ml of n-butanol, 10 ml of propylene oxide are added and the precipitate is filtered off. Recrystallisation from water/acetone 1:1 yields E-2-amino-5-phosphino-3-pentenoic acid butyl ester, m.p. 160°-161°.

EXAMPLE 6 a) 2.0 g of E-2-amino-5-phosphono-3-pentenoic acid are placed in 50 ml of ethanol and the whole is saturated with hydrogen chloride gas for 2½ hours at 50°. After concentration, the residue is dissolved in 18 ml of ethanol, 18 ml of propylene oxide are added and the precipitate is filtered off. Recrystallisation from water/ethanol 1:3 yields 2-amino-5-phosphono-3-pentenoic acid ethyl ester, m.p. 167°-168°.

b) 2.0 g of E-2-amino-5-phosphono-3-pentenoic acid are suspended in 40 ml of n-butanol and the suspension is saturated with hydrogen chloride gas for 3 hours at 40°. After concentration, the residue is dissolved in 30 ml of n-butanol, 15 ml of propylene oxide are added and the precipitate is filtered off. Recrystallisation from water/acetone 1:1 yields E-2-amino-5-phosphono-3-pentenoic acid butyl ester, m.p. 160°-161°.

c) 2.0 g of E-2-amino-5-phosphono-3-pentenoic acid are suspended in 30 ml of n-octanol and the suspension is saturated with hydrogen chloride gas for 4 hours at 70°. The mixture is concentrated in vacuo at 70° to half its volume, 50 ml of diethyl ether and 15 ml of propylene oxide are added and the whole is filtered. Recrystallisation from water/acetone 1:1 yields E-2-amino-5-phosphono-3-pentenoic acid octyl ester, m.p. 161°–162°.

d) 2.0 g of 2-amino-5-phosphono-3-pentenoic acid are suspended in 15 ml of 1-dodecanol and 25 ml of tetrahydrofuran and the suspension is saturated with hydrogen chloride gas for 4 hours at 50°. The mixture is freed of tetrahydrofuran in vacuo at 50°, 40 ml of acetone and 20 ml of propylene oxide are added and the whole is filtered. There is obtained from water/acetone 1:1, after stirring, E-2-amino-5-phosphono-3-pentenoic acid dodecyl ester, m.p. 158°–159°.

e) 1.5 g of E-2-amino-5-phosphono-3-pentenoic acid are suspended in 30 ml of n-propanol and the suspension is saturated with hydrogen chloride gas for 2½ hours at 50°. After concentration, the residue is dissolved in 15 ml of n-propanol, 15 ml of propylene oxide are added and the precipitate is filtered off. Recrystallisation from water/acetone 1:3 yields E-2-amino-5-phosphono-3-pentenoic acid propyl ester, m.p. 161°–162°.

f) 1.5 g of 2-amino-5-phosphono-3-pentenoic acid are suspended in 30 ml of n-pentanol and the suspension is saturated with hydrogen chloride gas for 3 hours at 50°. After concentration, the residue is dissolved in 15 ml of n-pentanol, 15 ml of propylene oxide are added and the precipitate is filtered off. Recrystallisation from water/acetone 1:1 yields E-2-amino-5-phosphono-3-pentenoic acid pentyl ester, m.p. 160°–161°.

g) 1.5 g of E-2-amino-5-phosphono-3-pentenoic acid are suspended in 30 ml of isobutanol and the suspension is saturated with hydrogen chloride gas for 3½ hours at 70°. After concentration, the residue is dissolved in 10 ml of isobutanol, 10 ml of propylene oxide are added and the precipitate is filtered off. Recrystallisation from water/acetone 1:1 yields E-2-amino-5-phosphono-3-pentenoic acid isobutyl ester, m.p. 163°–164°.

h) 1.5 g of E-2-amino-5-phosphono-3-pentenoic acid are suspended in 30 ml of sec.-butanol and the suspension is saturated with hydrogen chloride gas for 4 hours at 75°. After concentration, the residue is dissolved in 10 ml of 2-butanol, 10 ml of propylene oxide are added and the precipitate is filtered off. Recrystallisation from water/acetone 1:1 yields E-2-amino-5-phosphono-3-pentenoic acid sec.-butyl ester, m.p. 169°–170°.

EXAMPLE 7

E-2-amino-4-methyl-5-phosphono-3-pentenoic acid is obtained by hydrolysis of E-2-formylamino-4-methyl-5-dimethyl-phosphono-3-pentenoic acid ethyl ester in a manner analogous to that described in Example 1. For $^1$H-NMR see Example 18. E-2-amino-4-methyl-5-methylphosphono-3-pentenoic acid, m.p. 149°–150°, is obtained as a byproduct in preliminary fractions.

The starting material is manufactured as follows:

By reaction of 2-formylamino-3-hydroxy-4-methyl-4-pentenoic acid ethyl ester with thionyl bromide and subsequent treatment with trimethyl phosphite in a manner analogous to that described in Example 1, E-2-formylamino-4-methyl-5-dimethylphosphono-3-pentenoic acid ethyl ester is obtained in the form of a pale yellow oil.

EXAMPLE 8 a) 2.0 g of E-2-amino-4-methyl-5-phosphono-3-pentenoic acid are placed in 50 ml of ethanol and the whole is saturated with hydrogen chloride gas for 2½ hours at 50°. After concentration, the residue is dissolved in 20 ml of ethanol, 20 ml of propylene oxide are added and the precipitate is filtered off. Recrystallisation from water/ethanol (1:3) yields E-2-amino-4-methyl-5-phosphono-3-pentenoic acid ethyl ester, m.p. 193°–194°.

The following esters are obtained in an analogous manner:

b) E-2-amino-4-methyl-5-phosphono-3-pentenoic acid methyl ester, m.p. 193°–194° [water/acetone (9:1)];

c) E-2-amino-4-methyl-5-phosphono-3-pentenoic acid n-propyl ester, m.p. 184°–185°, (water);

d) E-2-amino-4-methyl-5-phosphono-3-pentenoic acid n-butyl ester, m.p. 186°–187°, [water/acetone (2:1)];

e) E-2-amino-4-methyl-5-phosphono-3-pentenoic acid isobutyl ester, m.p. 181°–182°, [water/acetone (9:1)];

f) E-2-amino-4-methyl-5-phosphono-3-pentenoic acid n-pentyl ester, m.p 207°–208°;

g) E-2-amino-4-methyl-5-phosphono-3-pentenoic acid n-hexyl ester, m.p. 207°–208°.

EXAMPLE 9

21 g of E-2-formylamino-4-methyl-5-O-ethyldiethoxymethylphosphonyl-3-pentenoic acid ethyl ester are stirred for 16 hours at 80° with 400 ml of 4.35N hydrochloric acid and the whole is subsequently concentrated in vacuo at 45°. The residue is dissolved in 100 ml of ethanol and 30 ml of propylene oxide are added, and the product is filtered off. Recrystallisation from water yields E-2-amino-4-methyl-5-phosphino-3-pentenoic acid, m.p. 176°–177°.

The starting material is manufactured as follows:

50 g of 2-formylamino-3-hydroxy-4-methyl-4-pentenoic acid ethyl ester in 500 ml of dry tetrahydrofuran are cooled to −78°. 89 g of thionyl chloride are added dropwise thereto in such a manner that the reaction temperature does not exceed −70°. Subsequently, the reaction solution is warmed to −10° within a period of 3 hours and is stirred for 3 hours at that temperature and then concentrated under a high vacuum at 20°.

The residue is taken up in 400 ml of dichloromethane and neutralised with saturated aqueous sodium hydrogen carbonate solution. The organic extracts are dried over sodium sulphate and concentrated by evaporation in vacuo at 30°. The residue is prepurified by column chromatography (silica gel, ethyl acetate) and the light-yellow oil that remains is dissolved in 30 ml of toluene. After the addition of 94 g of diethoxymethylphosphonous acid ethyl trimethylsilyl ester, the whole is stirred for 16 hours at 90°. The dark-yellow solution is poured onto ice/water, neutralised with sodium hydrogen carbonate and extracted with dichloromethane. The organic extracts are dried over sodium sulphate and concentrated by evaporation in vacuo at 30°. Purification of the residue by column chromatography (silica gel, ethyl acetate, then ethyl acetate/methanol 9:1) yields E-2-formylamino-4-methyl-5-O-ethyl-diethoxymethylphosphonyl-3-pentenoic acid ethyl ester in the form of a light-yellow oil, $^1$H-NMR (CDCl$_3$): 2.64 (dd, 2H, C(5)—H); 4.60 (d, 1H, P—CH); 5.26 (m, 2H, C(2)—H and c(3)—H).

EXAMPLE 10

Racemate separation of E-2-amino-4-methyl-5-phosphono-3-pentenoic acid.

A solution of 1.5 ml of phenylacetyl chloride in 25 ml of 1,4-dioxan is added at 20°, within a period of 20 minutes, to 209 mg of E-2-amino-4-methyl-5-phosphono-3- pentenoic acid in 21 ml of 2N sodium hydroxide solution while stirring vigorously, and the whole is stirred for 4 hours at room temperature. The reaction solution is poured onto 250 ml of water and repeatedly extracted with dichloromethane. The aqueous phase is concentrated to 20 ml in vacuo at 40°, pre-purified by ion exchange chromatography (DOWEX 50 W×8/water/1,4-dioxan 3:1) and concentrated in vacuo at 40°. The resulting E-2-phenylacetylamino-4-methyl-5-phosphono-3-pentenoic acid is adjusted to pH 7.5 in 150 ml of water with 2N sodium hydroxide solution and stirred for 16 hours at 37° with 250 mg of EUPERGIT-ACYLASE. After filtering in vacuo at 40°, the mixture is concentrated to 10 ml and separated by ion exchange chromatography (DOWEX 50 W×8/water) into (D)-E-2-phenylacetylamino-4-methyl-5-phosphono-3-pentenoic acid and into (L)-E-2-amino-4-methyl-5-phosphono-3-pentenoic acid.

a) The aqueous phases of (L)-E-2-amino-4-methyl-5-phosphono-3-pentenoic acid are concentrated in vacuo and the residue is purified by recrystallisation from water, m.p. 196°, $[\alpha]_D^{20} = +97.1 + 1.9°$ (c=0.5; water).

b) The aqueous phases of (D)-E-2-phenylacetylamino-4-methyl-5-phosphono-3-pentenoic acid are concentrated in vacuo and the residue is stirred for 3.5 hours at 85° with 25 ml of 4.35N hydrochloric acid and then repeatedly extracted with dichloromethane. Concentration of the aqueous phases in vacuo and purification of the residue by ion exchange chromatography yield (D)-E-2-amino-4-methyl-5-phosphono-3-pentenoic acid, m.p. 194°, $[\alpha]_D^{20} = -96.7 + 1.2°$ (c=0.8; water).

EXAMPLE 11

2..5 g of E-2-formylamino-5-O-ethyl-methylphosphonyl-4-methyl-3-pentenoic acid ethyl ester are heated for 26 hours under nitrogen at 80° in 200 ml of 4.35N hydrochloric acid. The whole is concentrated by evaporation in vacuo and the residue is dissolved, in each case twice, in 200 ml each of water, tetrahydrofuran and ethanol, the solutions each time being concentrated by evaporation in vacuo. Dissolving in 150 ml of ethanol, the addition of 5 ml of propylene oxide in 100 ml of tetrahydrofuran/ethanol (1:1) at 0° within a period of 20 minutes, filtration of the precipitate and drying for 45 hours at 50° in vacuo yield crude E-2-amino-4-methyl-5-methylphosphonyl-3-pentenoic acid, which is purified by chromatography on 20 g of Dowex 50 W×8 (H$_2$O) (amorphous white powder), $^1$H-NMR (D$_2$O): 1.20 (d, 3H, CH$_3$—P); 1.75 (d, 3H, CH$_3$); 2.45 (d, 2H, C(5)—H); 4.50 (d, 1H, C(2)—H); 5.15 (m, 1H, C(3)—H).

The starting material is manufactured by reaction of 2-formylamino-3-hydroxy-4-methyl-4-pentenoic acid ethyl ester with thionyl bromide in the manner described in Example 2 and subsequent treatment with methylphosphonous acid diethyl ester instead of triethyl phosphite.

EXAMPLE 12

14.5 g of E-2-formylamino-2-methyl-5-diethylphosphono-3-pentenoic acid methyl ester are heated for 32 hours under nitrogen at 100°–105° in 500 ml of 4.35N hydrochloric acid. Working up as in Example 11 yields E-2-amino-2-methyl-5-phosphono-3-pentenoic acid, m.p. 225°–226° (from water).

The starting material is manufactured as follows:

A solution of 14.1 g of 2-isocyanopropionic acid methyl ester and 8.5 g of freshly distilled acrolein in 50 ml of tetrahydrofuran is added within a period of 20 minutes at 0°–5° under nitrogen to a solution of 17 g of anhydrous zinc chloride in 75 ml of tetrahydrofuran, and the whole is stirred for 45 hours at 0°–5°. The whole is poured onto 500 ml of 10% sodium hydrogen carbonate solution and extracted with 200 ml of dichloromethane. The organic phase is dried over sodium sulphate and concentrated by evaporation. Filtration of the residue over silica gel (ethyl acetate as eluant) yields 4-methyl-5-vinyl-2-oxazoline-4-carboxylic acid methyl ester. By hydrolysis of the 4-methyl-5-vinyl-2-oxazoline-4-carboxylic acid methyl ester in a manner analogous to that described in Example 1, 2-formylamino-2-methyl-3-hydroxy-4-pentenoic acid methyl ester is obtained. By reaction of the 2-formylamino-3-hydroxy-2-methyl-4-pentenoic acid methyl ester with thionyl bromide and subsequent treatment with triethyl phosphite in the manner described in Example 1, E-2-formylamino-2-methyl-5-diethylphosphono-3-pentenoic acid methyl ester is obtained in the form of a yellow oil:

Calculated C: 46.91%; H: 7.22%; N: 4.56%; P: 10.08%;

Found C: 46.1%; H: 7.3%; N: 4.1%; P: 10.6%.

EXAMPLE 13

6.3 g of E-2-formylamino-3-methyl-5-diethylphosphono-3-pentenoic acid ethyl ester are heated for 30 hours at 100°–100° under nitrogen in 400 ml of 4.35N hydrochloric acid. Working up as in Example 11 yields E-2-amino-3-methyl-5-phosphono-3-pentenoic acid in the form of a white powder, m.p. 168°, $^1$H-NMR (D$_2$O): 1.50 (d, 3H, CH$_3$); 2.4 (m, 2H, CH$_2$); 4.30 (s, 1H, C(2)—H); 5.60 (m, 1H, C(4)—H).

The starting material is manufactured as follows: 5-Methyl-5-vinyl-2-oxazoline-4-carboxylic acid ethyl ester, b.p. 65°–75° (13 Pa) is obtained by reaction of isocyanoacetic acid ethyl ester with methyl vinyl ketone in a manner analogous to that described in Example 30. By hydrolysis of the 5-methyl-5-vinyl-2-oxazoline-4-carboxylic acid ethyl ester in a manner analogous to that described in Example 1, 2-formylamino-3-hydroxy-3-methyl-4-pentenoic acid ethyl ester is obtained. Reaction of the 2-formylamino-3-hydroxy-3-methyl-4-pentenoic acid ethyl ester with thionyl bromide and subsequent treatment with triethyl phosphite in a manner analogous to that described in Example 1 yields E-2-formylamino-3-methyl-5-diethylphosphono-3-pentenoic acid ethyl ester in the form of a colourless liquid.

EXAMPLE 14

E-2-formylamino-5-diethylphosphono-5-methyl-3-pentenoic acid ethyl ester is hydrolysed with 4.35N hydrochloric acid in the manner described in Example 11. E-2-amino-5-methyl-5-phosphono-3-pentenoic acid is isolated in the form of an amorphous white solid mass. $^1$H-NMR (D$_2$O): 1.05 (dd, 3H, CH$_3$); 2.45 (m, 1H, C(5)—H); 4.33 (d, 2H, C(2)—H); 5.5 and 5.9 (2m, 2H, C(3)—H and C(4)—H).

The starting material is manufactured as follows: Reaction of crotonaldehyde with isocyanoacetic acid ethyl ester in a manner analogous to that described in Example 1 yields 5-(propen-1-yl)-2-oxazoline-4-carboxylic acid ethyl ester. By hydrolysis of the 5-(propen-1-yl)-2-oxazoline-4-carboxylic acid ethyl ester analogously to Example 1, 2-formylamino-3-hydroxy-4-hexenoic acid ethyl ester is obtained. Reaction of the 2-formylamino-3-hydroxy-4-hexenoic acid ethyl ester with thionyl bromide and subsequent treatment with triethyl phosphite in a manner analogous to that described in Example 1 (12 hours) yields E-2-formylamino-5-diethylphosphono-5-methyl-3-pentenoic acid ethyl ester.

EXAMPLE 15

Hydrolysis of E-2-formylamino-4-ethyl-5-dimethylphosphono-3-pentenoic acid ethyl ester in a manner analogous to that described in Example 11 yields E-2-amino-4-ethyl-5-phosphono-3-pentenoic acid, m.p,. 17620 ($H_2O$).

The starting material is manufactured as follows: Reaction of 2-methylene-butyraldehyde with isocyanoacetic acid ethyl ester in a manner analogous to that described in Example 1 yields 5-(buten-2-yl)-2-oxazoline-4-carboxylic acid ethyl ester. A solution of 16 g of 5-(buten-2-yl)-2-oxazoline-4-carboxylic acid ethyl ester in 100 ml of ethanol/water (1:1) is heated at the boil, under reflux, for 15 hours. The whole is concentrated by evaporation in vacuo, the residue is taken up in 200 ml of dichloromethane, dried over sodium sulphate and filtered, and the filtrate is concentrated by evaporation to yield 2-formylamino-3-hydroxy-4-ethyl-4-pentenoic acid ethyl ester.

Reaction of the 2-formylamino-3-hydroxy-4-ethyl-4-pentenoic acid ethyl ester with thionyl bromide and subsequent treatment with trimethyl phosphite in a manner analogous to that described in Example 1 yields E-2-formylamino-4-ethyl-5-dimethylphosphono-3-pentenoic acid ethyl ester.

EXAMPLE 16

Hydrolysis of E-2-formylamino-4-propyl-5-dimethylphosphono-3-pentenoic acid ethyl ester in a manner analogous to that described in Example 11 yields E-2-amino-4-propyl-5-phosphono-3-pentenoic acid, m.p 193° ($H_2O$).

The starting material is manufactured as follows: Reaction of 2-methylene-pentanal with isocyanoacetic acid ethyl ester analogously to Example 1 yields 5-(penten-2-yl)-2-oxazoline-4-carboxylic acid ethyl ester. By hydrolysis of the 5-(penten-2-yl)-2-oxazoline-4-carboxylic acid ethyl ester in a manner analogous to that described in Example 15, 2-formylamino-3-hydroxy-4-propyl-4-pentenoic acid ethyl ester is obtained. Reaction of the 2-formylamino-3-hydroxy-4-propyl-4-pentenoic acid ethyl ester with thionyl bromide and subsequent treatment with trimethyl phosphite in a manner analogous to that described in Example 1 yields E-2-formylamino-4-propyl-5-dimethylphosphono-3-pentenoic acid ethyl ester.

EXAMPLE 17

Hydrolysis of E-2-formylamino-4-butyl-5-dimethylphosphono-3-pentenoic acid ethyl ester in a manner analogous to that described in Example 11 yields E-2-amino-4-butyl-5-phosphono-3-pentenoic acid, m.p. 186°–187°. ($H_2O$).

The starting material is manufactured as follows: Reaction of 2-methylene-hexanal with isocyanoacetic acid ethyl ester analogously to Example 1 yields 5-(hexen-2-yl)-2-oxazoline-4-carboxylic acid ethyl ester, which is hydrolysed in a manner analogous to that described in Example 15 to 2-formylamino-3-hydroxy-4-butyl-4-pentenoic acid ethyl ester. Reaction of the 2-formylamino-3-hydroxy-4-butyl-4-pentenoic acid ethyl ester with thionyl bromide and subsequent treatment with trimethyl phosphite analogously to Example 1 yields E-2-formylamino-4-butyl-5-dimethylphosphono-3-pentenoic acid ethyl ester.

EXAMPLE 18

Hydrolysis of E-2-formylamino-4-isopropyl-5-dimethylphosphono-3-pentenoic acid ethyl ester analogously to Example 11 yields E-2-amino-4-isopropyl-5-phosphono-3-pentenoic acid, m.p. 201° ($H_2O$).

The starting material is manufactured as follows: Reaction of 3-methyl-2-methylene-tutanal with isocyanoacetic acid ethyl ester analogously to Example 1 yields 5-(3-methyl-buten-2-yl)-2-oxazoline-4-carboxylic acid ethyl ester, which is hydrolysed analogously to Example 15 to 2-formylamino-3-hydroxy-4-isopropyl-4-pentenoic acid ethyl ester. Subsequent treatment with thionyl bromide followed by reaction with trimethyl phosphite analogously to Example 1 yields E-2-formylamino-4-isopropyl-5-dimethylphosphono-3-pentenoic acid ethyl ester.

EXAMPLE 19

3.9 g of E-2-formylamino-4-tert.-butyl-5-dimethylphosphono-3-pentenoic acid ethyl ester are hydrolysed analogously to Example 12. Separation by ion exchange chromatography (Dowex W 50, $H_2O$) yields 1.8 g of E-2-amino-4-tert.-butyl-5-phosphono-3-pentenoic acid and 0.075 g of Z-2-amino-4-tert.-butyl-5-phosphono-3-pentenoic acid.

E-isomer: M.p. 252°–253° ($H_2O$); $^1$H-NMR ($D_2O$): 0.95 (s, 9H, ($CH_3$)$_3$C); 2.65 (m, 2H, $CH_2$); approximately 4.7 (d, 1 H, C(2)—H); 5.33 (m, 1 H, C(3)—H).

Z-isomer: $^1$H-NMR ($D_2O$): 1.08 (s, 9H, ($CH_3$)$_3$C); 2.45 (m, 2H, $CH_2$); 4.95 (d, 1 H, C(2)—H); 5.20 (m, 1 H, C(3)—H).

The starting material is manufactured as follows: Reaction of 3,3-dimethyl-2-methylene-butanal with isocyanoacetic acid ethyl ester in a manner analogous to that described in Example 1 yields 5-(3,3-dimethylbuten-2-yl)-2-oxazoline-4-carboxylic acid ethyl ester, which is hydrolysed analogously to Example 17 to 2-formylamino-3-hydroxy-4-tert.-butyl-4-pentenoic acid ethyl ester. Subsequent reaction with thionyl bromide followed by treatment with trimethyl phosphite analogously to Example 1 yields E-2-formylamino-4-tert.-butyl-5-dimethylphosphono-3-pentenoic acid ethyl ester.

EXAMPLE 20

0.44 g of E-2-formylamino-4-benzyl-5-diethylphosphono-3-pentenoic acid ethyl ester are dissolved in 8 ml of 4.5N hydrochloric acid and heated at 85° for 48 hours. After concentration in vacuo, the residue is dissolved in a small amount of ethanol and 1 ml of ethanol/propylene oxide (1:1) is added dropwise thereto. The resulting white precipitate is filtered off and, after recrystallisation from water, E-2-amino-4-benzyl-5-phosphono-3-pentenoic acid is obtained in the form of colourless needles, m.p. 196°–198°.

The starting material is manufactured as follows: By reaction of isocyanoacetic acid ethyl ester with 2-benzyl-propenal in a manner analogous to that described in Example 1 and after purification by column chromatography (silica gel; dichloromethane/ethyl acetate 98:2), 5-(3-phenyl-propen-2-yl)-2-oxazoline-4-carboxylic acid ethyl ester is obtained in the form of a colourless oil, $^1$H-NMR (CDCl$_3$): 3.33 (s, 2H, $CH_2$); 4.37 (dd, 1H, C(4)—H); 4.87 (s, 1H); 5.07 (dd, 1H, C(5)—H); 5.16 (s, 1H).

By hydrolysis of the 5-(3-phenyl-propen-2-yl)-2-oxazoline-4-carboxylic acid ethyl ester in a manner analogous to that described in Example 1, 2-formylamino-3-hydroxy-4-benzyl-4-pentenoic acid ethyl ester is obtained, m.p. 87°–89°.

By reaction of 2-formylamino-3-hydroxy-4-benzyl-3-pentenoic acid ethyl ester with thionyl bromide and subsequent treatment with triethyl phosphite at 100° in a manner analogous to that described in Example 1, and after chromatography (silica gel; ethyl acetate), E-2-formylamino-4-benzyl-5-diethylphosphono-3-pentenoic acid ethyl ester is obtained in the form of a colourless oil, $^1$H-NMR (CDCl$_3$): 2.45 (d, 2H, C(5)—H); 3.80 (s, 1H, CH$_2$); 5.51 (m, 1H, C(3)—H).

EXAMPLE 21

0.15 g of E-2-formylamino-4-phenyl-5-diethylphosphono-3-pentenoic acid methyl ester are dissolved in 10 ml of 4.5N hydrochloric acid and heated at 75° for 192 hours. After concentration in vacuo, the foamy residue is dissolved in a small amount of ethanol and 1 ml of ethanol/propylene oxide (1:1) is added dropwise thereto. The resulting white precipitate is filtered off and recrystallised from water/acetone (1:2). E-2-amino-4-phenyl-5-phosphono-3-pentenoic acid is thus obtained in the form of colourless needles, m.p. 230°–233°.

The starting material is manufactured as follows:

By reaction of isocyanoacetic acid methyl ester with 2-phenylacrolein in a manner analogous to that described in Example 1, and after purification by column chromatography (silica gel; dichloromethane/methanol 97.5:2.5), 5-(1-phenyl-vinyl)-2-oxazoline-4-carboxylic acid methyl ester is obtained in the form of a pale yellow oil. $^1$H-NMR (CDCl$_3$) 3.80 (s, 3H, CH$_3$); 4.45 (dd, 1H, C(4)—H); 5.76 (d, 1H, C(5)—H).

By hydrolysis of the 5-(1-phenyl-vinyl)-2-oxazoline-4-carboxylic acid methyl ester in a manner analogous to that described in Example 1, 2-formylamino-3-hydroxy-4-phenyl-4-pentenoic acid methyl ester is obtained, m.p. 173°–174°.

By reaction of the 2-formylamino-3-hydroxy-4-phenyl-4-pentenoic acid methyl ester with thionyl bromide and subsequent treatment with triethyl phosphite in a manner analogous to that described in Example 1, and after chromatography (silica gel; ethyl acetate/hexane 4:1), E-2-formylamino-4-phenyl-5-diethylphosphono-3-pentenoic acid methyl ester is obtained in the form of a colourless oil. $^1$H-NMR (CDCl$_3$) 2.98 (d, 2H, C(5)—H); 5.03 (dd, 1H, C(2)—H); 5.77 (dd, 1H, C(3)—H).

EXAMPLE 22

At 0°, 170 mg of sodium hydrogen carbonate and, within a period of 5 minutes, 50 microliters of acetic anhydride are added to a solution of 100 mg of E-2-amino-5-phosphono-3-pentenoic acid in 6 ml of dioxan/water (1:1). The whole is stirred for 30 minutes at 0°, approximately 2 ml of Dowex 50 H$^+$ are added and filtration is carried out. The filtrate is concentrated by evaporation and purified by ion exchange chromatography (Dowex 50 H$^+$). Lyophilisation of the pure fractions yields 110 mg of E-2-acetamino-5-phosphono-3-pentenoic acid, m.p. 155°.

EXAMPLE 23

E-2-amino-4-methyl-5-phosphono-3-pentenoic acid ethyl ester a) 5-(2-propenyl)-oxazoline-4-carboxylic acid ethyl ester (1)

1.6 g of red copper(I) oxide are introduced into 200 ml of benzene. A solution of 140 g of isocyanoacetic acid ethyl ester and 105 g of freshly distilled methacrolein in 200 ml of benzene is added dropwise to this suspension within a period of 10 minutes with vigorous stirring, during which time the reaction temperature is kept at between 30° and 32° by cooling with ice. When the addition is complete, the mixture is kept at 30°–32° until the exothermic reaction subsides, and is then stirred at room temperature for one hour. After excess copper(I) oxide has been filtered off, the filtrate is concentrated by evaporation in vacuo at 30°. 600 ml of ether are added to the residue, which is then filtered over Celite and concentrated to dryness by evaporation in vacuo. In this manner, 5-(2-propenyl)-2-oxazoline-4-carboxylic acid ethyl ester is obtained in the form of a colourless oil having a boiling point of 110°–130° (5.3 Pa).

b) E-2-formylamino-3-hydroxy-4-methyl-4-pentenoic acid ethyl ester (2)

139 g of 5-(2-propenyl)-2-oxazoline-4-carboxylic acid ethyl ester are dissolved in 70 ml of tetrahydrofuran, and 27.4 g of water and 3.5 g of triethylamine are added thereto. The reaction mixture is stirred at 65°–70° for 62 hours and, after cooling, is taken up in 200 ml of dichloromethane. The solution is dried over 200 g of magnesium sulphate, filtered and concentrated by evaporation in vacuo. Purification of the viscous oil which remains by column chromatography (silica gel; hexane/ethyl acetate 3:2) yields 2-formylamino-3-hydroxy-4-methyl-4-pentenoic acid ethyl ester in the form of a diastereoisomeric mixture having a melting point of 67°.

c) E-2-formylamino-4-methyl-5-diisopropylphosphono-3-pentenoic acid ethyl ester (3)

Under an argon atmosphere, 18.6 ml of thionyl bromide are added dropwise at 20°, within a period of 5 minutes, to a solution of 40.20 g of crude 2-formylamino-3-hydroxy-4-methyl-4-pentenoic acid ethyl ester in 600 ml of 1,2-dichloroethane (slight cooling). After stirring for two hours at room temperature, 400 ml of water are added, the first 50 ml being slowly added dropwise. The mixture is stirred thoroughly for a further 15 minutes to complete the reaction. The organic phase is separated off and washed three times with ice-water and once with ice/saturated potassium bicarbonate solution (pH approximately 7.5). Drying over sodium sulphate and removal of the 1,2-dichloroethane by distillation in vacuo at 35° yields the crude bromide as intermediate, to which 160 ml of triisopropyl phosphite are added at room temperature, and the mixture is then stirred at 75° (bath temperature) under a partial vacuum (approximately 13 kPa) for 17 hours. The excess triisopropyl phosphite and other volatile by-products are then distilled off under a high vacuum (bath temperature 90°). Chromatography of the residue on ten times the amount by weight of silica gel (particle size 0.04–0.06 mm) using ethyl acetate as eluant yields E-2-formylamino-4-methyl-5-diisopropylphosphono-3-pentenoic acid ethyl ester in the form of a light-yellow honey, IR (CH$_2$Cl$_2$): 3410 (NH); 1740 (CO ester); 1690 (CO amide); 1235 (P=O); 980–1015 (P—O—C).

d) E-2-amino-4-methyl-5-phosphono-3-pentenoic acid ethyl ester (4)

56.7 ml of trimethylbromosilane are added dropwise within a period of 15 minutes at 20° to a solution of 25.42 g of E-2-formylamino-4-methyl-5-diisopropylphosphono-3-pentenoic acid ethyl ester in 102 ml of dry dichloromethane. After stirring at room temperature for 20 hours, 102 ml of ethanol are added dropwise within a period of 15 minutes, and the whole is stirred for a further 20 hours. The clear reaction solution is then completely concentrated by evaporation in vacuo. The residue is concentrated by evaporation a further three times in each case after the addition of 100 ml of toluene. The oily residue is dissolved in 102 ml of ethanol, and a solution of 102 ml of propylene oxide in 102 ml of ethanol is added dropwise thereto. The product, obtained in crystalline form, is filtered off after 2 hours (room temperature) and washed with ethanol and ether. After drying (80°, 4 hours) under a high vacuum, E-2-amino-4-methyl-5-phosphono-3-pentenoic acid ethyl ester is obtained in analytically pure form, m.p. 212° (decomp.).

EXAMPLE 24

E-2-amino-4-methyl-5-phosphono-3-pentenoic acid ethyl ester a) E-2-formylamino-4-methyl-5-dimethylphosphono-3-pentenoic acid ethyl ester (1)

100.5 g of 2-formylamino-3-hydroxy-4-methyl-4-pentenoic acid ethyl ester are dissolved in 1.5 liters of dichloroethane, and then 47 ml of thionyl bromide are added dropwise at 20°–25° and the mixture is stirred at room temperature for one hour. 750 ml of water are added to the reaction mixture, which is then stirred vigorously for 10 minutes. The organic phase is separated off, extracted with 1 liter of ice-water, 1 liter of 1N potassium hydrogen carbonate solution and a further 1 liter of ice-water, dried over magnesium sulphate and concentrated by evaporation. 50 ml of trimethyl phosphite are added directly to the resulting E-5-bromo-2-formylamino-4-methyl-3-pentenoic acid ethyl ester, a yellow oil, and the mixture is stirred at a bath temperature of 70° and approximately 15 kPa for 15 hours. The reaction mixture is degassed for 30 minutes under a water-jet vacuum and for one hour under a high vacuum at 40°–50°. The resulting product is taken up in 600 ml of water and extracted three times with 500 ml of ethyl acetate each time. The combined organic phases are washed twice with 300 ml of water each time. All the aqueous phases are combined, saturated with sodium chloride and extracted three times with 500 ml of dichloromethane each time. The combined organic phases are dried over magnesium sulphate and concentrated by evaporation. The product is chromatographed over silica gel (ethyl acetate/isopropanol 7:2). In this manner, E-2-formylamino-4-methyl-5-dimethylphosphono-3-pentenoic acid ethyl ester is obtained in the form of a yellow oil, $^1$H-NMR (DMSO): 1.82 (d, 3H, 4—CH$_3$); 2.69 (d, 2H); 5.03 (m, 1 H); 5.32 (m, 1 H).

b) E-2-amino-4-methyl-5-phosphono-3-pentenoic acid ethyl ester (2)

16.9 g of E-2-formylamino-4-methyl-5-dimethylphosphono-3-pentenoic acid ethyl ester are dissolved in 80 ml of dichloromethane under a nitrogen atmosphere, and 30 ml of trimethylbromosilane are added dropwise at approximately 25° within a period of 30 minutes. The mixture is stirred at room temperature for 20 hours, and then 80 ml of ethanol are added dropwise at approximately 25° within a period of 30 minutes. The mixture is then again stirred at room temperature for 22 hours and is then concentrated by evaporation. The residue is dissolved in 80 ml of ethanol, and 80 ml of propylene oxide in 80 ml of ethanol are added dropwise with slight cooling. The mixture is stirred at room temperature for one hour to complete the reaction, filtered and washed with ethanol and ether. In this manner there is obtained E-2-amino-4-methyl-5-phosphono-3-pentenoic acid ethyl ester, m.p. 215°–217° (decomp.).

EXAMPLE 25

E-2-amino-4-methyl-5-phosphono-3-pentenoic acid ethyl ester a) E-2-formylamino-4-methyl-5-di(2-chloroethyl)-phosphono-3-pentenoic acid ethyl ester (1)

8.2 g of E-5-bromo-2-formylamino-4-methyl-3-pentenoic acid ethyl ester and 19 ml of tris-(2-chloroethyl)-phosphite are stirred at a bath temperature of 70° for 20 hours. The resulting mixture is chromatographed on silica gel using ethyl acetate and ethyl acetate/isopropanol (7:1) as eluant, and the product is crystallised from ethyl acetate/diethyl ether. In this manner there is obtained E-2-formylamino-4-methyl-5-di(2-chloroethyl)phosphono-3-pentenoic acid ethyl ester, m.p. 47°–49°.

b) E-2-amino-4-methyl-5-phosphono-3-pentenoic acid ethyl ester (2)

In a manner analogous to that described in Example 24, using 3 g of E-2-formylamino-4-methyl-5-di(chloroethyl)phosphono-3-pentenoic acid ethyl ester, there is also obtained E-2-amino-4-methyl-5-phosphono-3-pentenoic acid ethyl ester, m.p. 215° (decomp.).

EXAMPLE 26

E-2-amino-4-phosphonomethyl-3,6-heptadienoic acid a) 2-methylene-4-pentenealdehyde (1) 24.5 g of a 37% aqueous formaldehyde solution are added to a mixture of 14.7 g of piperazine, 20.5 g of glacial acetic acid and 21.28 g of water, and the whole is stirred at room temperature for 10 minutes. While continuing stirring, 25.35 g of 4-pentenealdehyde are added, and the reaction mixture is heated at 75° for 3 hours. After cooling to room temperature, the organic phase is separated off and the aqueous phase is extracted three times with 50 ml of diethyl ether each time. The combined organic phases are washed three times with 50 ml of a saturated sodium bicarbonate solution each time, dried over magnesium sulphate and concentrated by evaporation in vacuo. Fractional distillation of the residue yields 2-methylene-4-pentenealdehyde in the form of a colourless oil, b.p. 65°/6.6 kPa.

b) 5-[2-(1,4-pentadienyl)]-2-oxazoline-4-carboxylic acid methyl ester (2)

By reaction of isocyanoacetic acid methyl ester with 2-methylene-4-pentenealdehyde in toluene in a manner analogous to that described in Example 23, and after subsequent purification by column chromatography (silica gel, ethyl acetate/hexane 1:4), 5-(2-(1,4-pentadienyl))-2-oxazoline-4-carboxylic acid methyl ester is obtained in the form of a colourless oil, $^1$H-NMR (CDCl$_3$): 2.80 (d, 2H, CH$_2$); 4.45 (dd, 1 H, C(4)—H); 5.82 (m, 1 H, C=CH—); 7.00 (d, 1 H, C(2)—H).

8.1 g of 5-(2-(1,4-pentadienyl))-2-oxazoline-4-carboxylic acid methyl ester are dissolved in 20 ml of tetrahydrofuran, and 10 ml of water are added thereto. The reaction mixture is stirred at 75° for 1.5 hours and, after cooling, is concentrated by evaporation in vacuo. Crystallisation of the resulting residue from isopropanol/hexane yields 2-formylamino-3-hydroxy-4-methylene-6-heptenoic acid methyl ester in the form of a diastereoisomeric mixture, m.p. 75°–77°.

c) E-2-formylamino-4-bromomethyl-3,6-heptadienoic acid methyl ester (3)

5.0 g of 2-formylamino-3-hydroxy-4-methylene-6-heptenoic acid methyl ester in 200 ml of dry tetrahydrofuran are cooled to −78°, and 20 ml of 1,5-hexadiene are added thereto. 9 ml of thionyl bromide are added slowly dropwise in such a manner that the reaction temperature does not exceed −50°. When the addition is complete, the reaction solution is heated to 0° within a period of approximately 3 hours and is stirred at that temperature for 3 hours. The solution is then poured onto 300 ml of a cold (5°–10°) saturated sodium bicarbonate solution and extracted with diethyl ether. The organic extracts are washed with saturated sodium chloride solution, dried over magnesium sulphate and concentrated by evaporation in vacuo. Purification by column chromatography (silica gel, ethyl acetate/hexane 1:1) yields E-2-formylamino-4-bromomethyl-3,6-heptadienoic acid methyl ester in the form of a colourless oil, $^1$H-NMR (CDCl$_3$): 3.20 (d, 2H, C(5)—H); 4.00 (s, 2H, CH$_2$Br).

d) E-2-formylamino-4-diethylphosphonomethyl-3,6-heptadienoic acid methyl ester (4)

3.7 g of E-2-formylamino-4-bromomethyl-3,6-heptadienoic acid methyl ester are dissolved in 37 ml of triethyl phosphite, and the mixture is heated at 75° for 8 hours. Excess triethyl phosphite is then distilled off under a high vacuum. Purification by column chromatography (silica gel, methanol/ethyl acetate 1:10) yields E-2-formylamino-4-diethylphosphonomethyl-3,6-heptadienoic acid methyl ester in the form of a colourless oil, $^1$H-NMR (CDCl$_3$): 2.54 (d, 2H, P—CH$_2$); 3.10 (m, 2H, C(5)—H); 5.10 (m, 2H, C(7)—H); 5.37 (d, 1 H, C(2)—H); 5.74 (m, 1 H, C(6)—H).

e) E-2-amino-4-phosphonomethyl-3,6-heptadienoic acid (5)

0.74 g of E-2-formylamino-4-diethylphosphonomethyl-3,6-heptadienoic acid methyl ester is dissolved in 12 ml of dichloromethane, and 0.7 ml of trimethyliodosilane is added dropwise thereto. After stirring at room temperature for 4 hours, 1N sodium thiosulphate solution is added until the colour of the reaction solution becomes lighter. 10 ml of a 4.5N hydrochloric acid solution are then added to the reaction mixture, which is then stirred at room temperature for 30 minutes. The aqueous phase is separated off, washed twice with 20 ml of dichloromethane each time, and concentrated by evaporation in vacuo. The residue is dissolved in 10 ml of 4.5N hydrochloric acid, stirred at room temperature for 16 hours, and then concentrated by evaporation in vacuo. The residue so obtained is taken up in 40 ml of ethanol and filtered until clear, and then 10 ml of propylene oxide/ethanol (1:1) are added dropwise. The resulting white precipitate is filtered off and purified by column chromatography (Dowex 50×8/H$_2$O). Concentration yields E-2-amino-4-phosphonomethyl-3,6-heptadienoic acid in the form of a white crystallisate, m.p. 154°–157°, $^1$H-NMR (D$_2$O): 2.64 (d, 2H, P—CH$_2$); 3.15 (m, 2H, C(5)—H); 5.20 (m, 2H, C(7)—H); 5.50 (dd, 1 H, C(3)—H); 5.90 (m, 1 H, C(6)—H).

EXAMPLE 27

(2R)-2-amino-4-methyl-5-phosphono-3-pentenoic acid a) (L)-N-tert.butoxycarbonyl-serine-N-methoxy-N-methyl-amide (1) 541.6 ml of N-methylmorpholine are added within 27 minutes at −20° to −25° to a solution of 1 kg of (L)-N-tert.butoxycarbonyl-serine in 1 liter of tetrahydrofurane. The reaction mixture is stirred for 15 minutes at this temperature. Then 699.6 ml of chloroformic acid isobutyl ester and subsequently 445,8 ml of N-methoxy-N-methylamine are added within 42 and 40, resp. minutes. The reaction mixture is allowed to warm to room temperature and evaporated to dryness. The residue is dissolved in 3 liters of ethyl acetate. The solution is extracted with 3.5 liters of 2n-hydrochloric acid and subsequently with 3 l of saturated aqueous sodium hydrogencarbonate solution. The water-layers are extracted with 3 liters of ethyl acetate. All organic extracts are combined, washed with 2 liters of saturated sodium dichloride solution, dried over magnesium sulfate and evaporated at 50° to dryness. The residue is triturated with 3.5 liters of hexane with ice-cooling. The resulting white precipitate is filtrated off, washed with 1 l of hexane and dried under reduced pressure to yield 781 g -1, m.p. 116°–117°; calculated for C$_{11}$H$_{20}$N$_2$O$_5$ C 48.38%, H 8.12% N 11.28%; found C 48.28%, H 8.02%, N 11.32%.

b) (L)-3-tert.butoxycarbonyl-2,2-dimethyl-oxazolidine-4-carboxylic acid-N-methoxy-N-methyl-amide (2)

A mixture of 781 g of 1, 3.3 liters of acetone dimethylacetal and 42 g of pyridinium(toluol-4-sulfonate) are warmed to 72° and refluxed for 17 hours. After addition of additional 20 g of pyridinium(toluol-4-sulfonate) heating to boil is continued for additional 9 hours while gradually distilling of approximately 750 ml of solvent and adding 700 ml of acetone dimethylacetal. All volatile constituents we distilled off. The residue is dessolved in 2 liters of diethyl ether and extracted twice with 1 liter and 0.5 liter of n-hydrochloric acid, once with 0.3 liter of saturated sodium hydrogencarbonate solution and once with 0.3 liter of saturated sodium chloride solution. The aqueous extracts we re-extracted twice with 0.5 liter either time of diethyl ether. All organic extracts are combined, dried over magnesium sulfate and evaporated to dryness. The residue is dissolved hot in a 9:1-mixture of hexane and diethyl ether. After addition of additional 600 ml of hexane and 50 ml of diethyl ether, the reaction mixture is cooled down while during crystallisation with 1.1 liter of hexane. The precipitate formed is filtered off, washed with hexane and dried under reduced pressure at 40° yielding 640 g of 2; m.p. 67°–68°; calculated for C$_{13}$H$_{24}$N$_2$O$_5$ C 54.15%, H 8.39%, N 9.72%; found C 53.96%, H 8.37%, N 9.91%.

c) (4S)-2,2-dimethyl-4-formyl-3-oxazolidine-carboxylic acid tert.butyl ester (3)

2.53 g of lithium aluminium hydride are added with cooling to maintain a temperature of 5° to 15° to 28.8 g of 2, dissolved in 350 ml of diethyl ether. After stirring at 5° for 1.5 hours a solution of 5.77 g of sodium hydrogen sulfate is added slowly to keep the reaction temperature at 15° (40 minutes). The suspensions formed is filtered clear and the solid portion is washed with ether. The filtrate is washed, with cooling, twice with 200 ml each of n-hydrochloric acid, twice with 150 ml each of 5% sodium hydrogencarbonate solution and with 100 ml of saturated sodium chloride solution. The aqueous extracts are re-extracted with ether and all organic extracts are combined, dried over sodium sulfate and evaporated. The residue is distilled at 0.4 mb yielding 17.78 g of 3; b.p. 85°-90°, $[\alpha]_D = -93°(c=1, CHCl_3)$; calculated for $C_{11}H_{19}NO_4$ C 57.63%, H 8.35% N 6.11%, O 27.91%; found C 57.59%, H 8.54%, N 6.17%, O 27.74%.

d) 3-((4'R)-N-tert.-butoxycarbonyl-2',2'-dimethyl-4'-oxazolidinyl)-2-methylpropenoic acid ethyl ester (4)

A solution of 39.5 g of (4S)-2,2-dimethyl-4-formyl-3-oxazolidinecarboxylic acid tert.-butyl ester 3 in 200 ml of dichloromethane is added dropwise within a period of 2 hours to a solution of 68.7 g of 1-ethoxycarbonylethylidenetriphenylphosphorane in 900 ml of dichloromethane. After stirring at room temperature for 6 hours, the mixture is cooled to 10° and there are then added dropwise within a period of 15 minutes 530 ml of a 10% aqueous sodium hydrogen phosphate solution. After stirring at 15° for 30 minutes, the organic phase is separated off and the aqueous phase is extracted with 250 ml of dichloromethane. The organic phases are dried over magnesium sulphate and concentrated by evaporation. The residue is stirred with 70 ml of ether. The suspension is filtered and the filtration residue is washed with ether. The filtrate is concentrated by evaporation and the residue is separated by chromatography on silica gel. Elution with hexane/ethyl acetate 9:1 yields, in addition to 2.32 g of cis-isomer and 2.21 g of mixed fraction (cis/trans = 38:62), 45.4 g of 4. $^1$H-NMR (60 MHz, CDCl$_3$, trans-isomer): inter alia 4.7 ppm (m, H—C(4')); 6.7 ppm (d, J=9, H—C(3)). $^1$H-NMR (60 MHz, CDCl$_3$, cis-isomer): inter alia 5.2 ppm (m H—C(4')); 6.08 ppm (d, J=7, H—C(3)).

e) (4R)-2,2-dimethyl-4-(3'-hydroxy-2'-methylprop-1'-enyl)oxazolidine-3-carboxylic acid tert.-butyl ester (5)

389 ml of a 1 molar solution of diisobutylaluminium hydride in hexane are added within a period of 15 minutes to a solution, cooled to 3°, of 48.7 g of 4 in 1 liter of dry diethyl ether. The temperature of the mixture is allowed to rise to 11°, and there are then added thereto, while cooling with ice, 100 ml of ethyl acetate followed by 50 ml of 2N sodium hydroxide solution. The temperature of the mixture is allowed to rise to approximately 28°, without cooling, and then a further 7 ml of 2N sodium hydroxide solution are added. The mixture is stirred at room temperature for 15 hours, and then sodium sulphate is added and the whole is filtered. Concentration of the filtrate by evaporation yields 42.1 g of crude 2. A sample (0.97 g) is purified by chromatography on 40 g of silica gel. Elution with hexane/ethyl acetate 3:1 yields 0.74 g of 5. $^1$H-NMR (300 MHz, DMSO-d$_6$): inter alia 3.52 (d×d, J=9 and 3) and 4.02 (d×d, J=9 and 6) (2H—C(5)); 3.78 (m, 2H—C(3')); 4.54 (m, H—C(4)); 4.81 (t, J=6, OH); 5.33 (d, J=9, H—C(1')).

f) (4R)-2,2-dimethyl-4-(3'-bromo-2'-methylprop-1'-enyl)oxazolidine-3-carboxylic acid tert.-butyl ester (6)

47.6 g of triphenylphosphine are added at 0° to a solution of 41.0 g of 5 and 60.2 g of tetrabromomethane in 1 liter of dry diethyl ether. After 30 minutes, the cooling bath is removed and the mixture is stirred at room temperature for 17 hours. 20 g of tetrabromomethane and 15.9 g of triphenylphosphine are added, and the mixture is stirred at room temperature for 2 hours. The white suspension is filtered and the filtration residue is washed with ether. The residue remaining after the filtrate has been concentrated by evaporation is chromatographed on 0.9 kg of silica gel. Elution with hexane/ethyl acetate 9:1 yields 30.59 g of 6, m.p. 62°-65° C. $^1$H-NMR (300 MHz, DMSO-d$_6$): inter alia 3.55 (d×d, J=9 and 2) and 4.04 (d×d, J=9 and 6) (2H—C(5)); 4.15 (m, 2H—C(3')); 4.49 (m, H—C(4)); 5.65 (d, J=9, H—C(1')).

g) (4R)-2,2-dimethyl 4-(3'-dimethylphosphono-2'-methylprop-1'-enyl)-oxazolidine-3-carboxylic acid tert.-butyl ester (7)

A solution of 13.4 g of 6 in 70 ml of trimethyl phosphite is stirred at 80° for 15 hours. The excess phosphite is evaporated off at 24 mbar. Drying of the residue under a high vacuum yields 14.3 g of crude 7. $^1$H-NMR (300 MHz, DMSO-d$_6$): inter alia 2.63 (d, J=23, 2H—C(3')); 3.59 (d, J=11, (CH$_3$O)$_2$PO).

h) N-((2R)-5-dimethylphosphono-1-hydroxy-4-methyl-3-penten-2-yl)-carbamic acid tert.-butyl ester (8)

7 g of Amberlyst® 15 (H$^+$ form, 20-50 mesh) are added to a solution of 14.0 g of 7 in 250 ml of methanol. The mixture is stirred at room temperature for 17 hours and filtered, and the filtrate is concentrated by evaporation. Chromatography of the residue on 0.33 kg of silica gel using ethyl acetate/methanol 10:1 as eluant yields 10.6 g of 8. $^1$H-NMR (300 MHz, DMSO-d$_6$): inter alia 4.60 (t, J=6, OH); 6.67 (d, J=7, NH).

i) (2R)-2-tert.-butoxycarbonylamino-5-dimethylphosphono-4-methyl-3-pentenoic acid (9)

i,a) Oxidation with chromosulphuric acid

To a solution of 0.323 g of 8 in 10 ml of acetone there is added 0.77 ml of a solution that is 3.25 molar in chromium trioxide and 5.29 molar in sulphuric acid. The mixture is stirred at room temperature for 40 minutes and then there are added 2 ml of isopropanol followed by 50 ml of ethyl acetate. 0.1 g of activated carbon is then added to the mixture. After 10 minutes, the mixture is filtered and washed with 50 ml of ethyl acetate. The filtrate is extracted three times with 50 ml of 10% sodium hydrogen carbonate solution each time. The aqueous phase is extracted twice with 40 ml of ethyl acetate each time, acidified to pH 1 using 2N hydrochloric acid, and then extracted three times with 70 ml of ethyl acetate each time. The organic extracts are washed with saturated sodium chloride solution, dried over magnesium sulphate and concentrated by evaporation. Chromatography on 8 g of silica gel using chloroform/methanol/acetic acid 18:1:1 as eluant yields 65 mg of 9. $^1$H-NMR (300 MHz, DMSO-d$_6$): 1.37 (s, (CH$_3$)$_3$CO); 1.82 (d, J=2, CH$_3$—C(4)); 2.63 (d, J=22, 2H—C(5)); 3.61 (d, J=11, (CH$_3$O)$_2$PO); 4.62 (t, J=8, H—C(2)); 5.25 (m, H—C(3)); 7.18 (d, J=8, NH); 11.7-12.5 (CO$_2$H).

i,b) Oxidation with oxygen/platinum

To a solution of 0.66 g of 8 and 0.2 g of sodium hydrogen carbonate in 20 ml of water and 2 ml of dioxane there is added a suspension of platinum prepared by hydrogenation of 313 mg of platinum oxide in 50 ml of water. In a cylindrical apparatus, oxygen is passed through the mixture from bottom to top at 55° by means of a glass frit, with vigorous stirring. The mixture is filtered and washed with water, and the filtrate is extracted five times with 100-150 ml of ethyl acetate each time. Concentration of the extracts by evaporation yields 220 mg of educt 5. 1 g of Amberlyst® 15 (strongly acidic) is added to the aqueous phase, which is then filtered and concentrated by evaporation in vacuo at 40°. Purification as in f,a) yields 156 mg of 9. $^1$H-NMR (300 MHz, CDCl$_3$): 1.43 (s, (CH$_3$)$_3$C); 1.96 (d, J=3 Hz, CH$_3$—C(4)); 2.55 and 2.71 (2 d×d, J=22 and 15, 2H—C(5)); 3.75 and 3.76 (2 d, J=11, 2 OCH$_3$); 4.97 (m, H—C(2)); 5.25–5.45 (m, NH and H—C(3)).

j) (2R)-2-amino-4-methyl-5-phosphono-3-pentenoic acid (10)

0.71 ml of trimethylsilyl bromide is added at 0° to a solution of 123 mg of 9 in 3 ml of dichloromethane. After stirring at 0° for 4 hours, 20 ml of water are added. After 30 minutes, the dichloromethane phase is separated off and washed three times with 15 ml of water each time. The aqueous phases are extracted three times with 20 ml of dichloromethane each time and concentrated by evaporation in vacuo. The residue is dissolved in 10 ml of 5N hydrochloric acid and is then stirred for 48 hours, diluted with 20 ml of water and extracted three times with 20 ml of dichloromethane each time. The aqueous phase is concentrated by evaporation in vacuo, and the residue is dried under a high vacuum and dissolved in 3 ml of etharol, and then approximately 1 ml of propylene oxide is added dropwise thereto. The suspension is filtered. Washing of the filtration residue with ethanol and drying under a high vacuum at room temperature yields 62 mg of 10, m.p. 165° C. (decomposition).

In order to analyse the purity of the enantiomer, a sample is derivatised to the amide with (R)-(+)-methoxytrifluoromethylphenylacetic acid chloride. $^1$H-NMR analysis (300 MHZ) by integration of the OCH$_3$ signals gives ≧95% (2R)-isomer (3.44 ppm) and ≦5% (2S)-isomer (3.37 ppm).

EXAMPLE 28

(2R)-2-E-amino-4-methyl-5-phosphono-3-pentenoic acid ethyl ester a) (4R)-2,2-dimethyl-4-(3'-diisopropylphosphono-2'-methylprop-1'-enyl)-oxazolidine-3-carboxylic acid tert.-butyl ester (1)

A solution of 6.68 g of bromide according to Example 27f in 14.8 ml of dry triisopropyl phosphite is heated at 70° C. for 17 hours under a pressure of 100 mbar. The mixture is concentrated by evaporation at 0.4 mbar/70°. Chromatography on 350 g of silica gel (eluant hexane/ethyl acetate 1:1) yields 8.28 g of 1, R$_f$ value=0.077.

b) N-((2R)-5-diisopropylphosphono-1-hydroxy-4-methyl-3-penten-2-yl)-carbamic acid tert.-butyl ester (2)

2.25 g of Amberlyst ® 15 (H$^+$ form, 20–50 mesh) are added to a solution of 4.49 g of phosphonic acid ester 1 according to a) in 100 ml of methanol. The mixture is stirred at room temperature for 2 days and is filtered, and the filtrate is concentrated by evaporation. Chromatography of the residue on 125 g of silica gel (eluant ethyl acetate/methanol 20:1) yields 2.44 g of 2.

c) (2R)-2-tert.-butoxycarbonylamino-5-diisopropylphosphono-4-methyl-3-pentenoic acid (3)

To a solution of 1.6 g of alcohol 2 according to b) in 60 ml of acetone there are added at 0°–5° 3.3 ml of a solution that is 3.25 molar in chromium(VI) oxide and 5.29 molar in sulphuric acid. The mixture is stirred at 0° for 6 hours and at room temperature for 12 hours. After the addition of 5 ml of isopropanol and 40 ml of 20% sodium chloride solution, the mixture is stirred for 10 minutes and is then extracted continuously with methyl acetate for 15 hours in a Kutscher-Steudel apparatus. The organic phase is dried over sodium sulphate and concentrated by evaporation, and the residue is chromatographed on 75 g of silica gel with hexane/ethyl acetate/acetic acid 16:10:1. This yields 0.92 g of 3, [α]$_D$=−94.5° (c=1.2, CHCl$_3$). $^1$H-NMR (300 MHz, CDCl$_3$): 1.2–1.3 (4d, (2-propo)$_2$); 1.4 (s, (CH$_3$)$_3$CO); 1.95 (d, J=3, CH$_3$—C(4)); 3.5 and 3.62 (2 d×d, J=23 and 15, 2H—C(5)); 4.66 (m, (2-propo)$_2$); 4.92 (m, H—C(2)); 5.30 (m, H—C(3)); 5.42 (d, J=7, NH); 9.0–10.0 (broad, CO$_2$H).

d) (2R)-2-tert.-butoxycarbonylamino-5-diisopropylphosphono-4-methyl-3-pentenoic acid ethyl ester (4)

0.09 g of 1-amino-1-chloro-N,N,2-trimethylpropene is added at 0°–5° to a solution of 0.2 g of acid 3 according to c) in 15 ml of dry dichloromethane. After stirring for 30 minutes at 0°, 0.4 g of pyridine in 5 ml of ethanol is added. The mixture is stirred further at 0° for 90 minutes and at room temperature for 15 hours, and is then diluted with 20 ml of dichloromethane and washed twice with 20 ml of water each time. The organic phase is dried using sodium sulphate, concentrated by evaporation and chromatographed on 25 g of silica gel. Elution with ethyl acetate/ methanol 10:1 yields 0.12 g of 4. $^1$H-NMR (300 MHz, CDCl$_3$): 1.2–1.4 (m, 2 (CH$_3$)$_2$CHO, CH$_3$CH$_2$O); 1.45 (s, (CH$_3$)$_3$CO); 1.98 (d, J=3, CH$_3$—C(4)); 2.55 (d, J=23, 2H—C(5)); 4.2 (m, CH$_3$CH$_2$O); 4.69 (m, 2 (CH$_3$)$_2$CHO); 5.0 (m, H—C(2)); 5.16 (m, H—C(3), NH).

e) (2R)-2-amino-4-methyl-5-phosphono-3-pentenoic acid ethyl ester (5)

0.11 ml of trimethtlsilyl bromide is added at 0° to a solution of 0.1 g of ester 4 according to d) in 10 ml of dichloromethane. The mixture is stirred at 0° for 4 hours and at room temperature for 15 hours. 20 ml of water are added, the mixture is stirred for 15 minutes, and then the aqueous phase is separated off and the water is evaporated off under a high vacuum. The residue is dissolved twice in 5 ml of ethanol each time, concentrated by evaporation and again dissolved in 5 ml of ethanol. 0.5 ml of propylene oxide is added. The precipitate is filtered off, washed with ethanol and dried under a high vacuum for 15 hours; 48 mg of 5, [α]$_D$=−75° (c=0.5, H$_2$O).

In order to analyse the purity of the enantiomer, a sample is derivatised to the amide dimethyl ester with (R)-(+)-methoxytrifluoromethylphenylacetic acid chloride followed by diazomethane. $^1$H-NMR analysis (300 MHz) by integration of the OCH$_3$ signals gives ≧97% (2R)-isomer (3.5 ppm) and ≦3% (2S)-isomer (3.37 ppm).

EXAMPLE 29

(2R)-2-amino-4-methyl-7-phosphono-3-heptenoic acid (10)

a) (4R)-2,2-dimethyl-4-(1'-hydroxy-2'-methylprop-2'-enyl)oxazolidine-3-carboxylic acid tert.-butyl ester (1)

45 ml of a 1.1 molar solution of isopropenylmagnesium bromide are added dropwise at 0°–5° within a period of 25 minutes to a solution of 6.9 g of (4S)-2,2-dimethyl-4-formyloxazolidine-3-carboxylic acid tert.-butyl ester (according to Example 27c)) in 60 ml of dry tetrahydrofuran. The mixture is stirred at 0° for 45 minutes, allowed to warm up to room temperature and cooled again to 10°, and then 90 ml of buffer solution (1 molar, phosphate, pH 7) are added. The mixture is filtered and the filtrate is extracted twice with 100 ml of ethyl acetate each time. The organic phase is washed twice with 50 ml of water each time and with saturated sodium chloride solution, and is dried with sodium sulphate. Removal of the solvent by evaporation yields 8 g of 1, a diastereoisomeric mixture. Separation may be effected by chromatography on silica gel using hexane/ethyl acetate 4:1 and yields crystalline (1'S)-threo-epimer (R$_f$ value 0.2) and (1'R)-erythro-epimer (R$_f$ value: 0.16) in a ratio of approximately 1:2.

b) (4R)-4-(1'-acetoxy-2'-methylprop-2'-enyl)-2,2-dimethyloxazolidine-3-carboxylic acid tert.-butyl ester (2)

60 ml of acetic anhydride are added dropwise at 0°–5° within a period of 10 minutes to a solution of 15.6 g of the epimer mixture according to a) in 60 ml of pyridine. The mixture is stirred at room temperature for 15 hours and diluted with 0.5 liter of diethyl ether, and then 200 ml of 2N hydrochloric acid are added while cooling with ice. The organic phase is washed with 250 ml of 2N hydrochloric acid and twice with 200 ml of 10% sodium carbonate solution each time. Drying over sodium sulphate and removal of the solvent by evaporation yields 15.4 g of 2.

c) (4R)-4-(4'-carboxy-2'-methylbutenyl)-2,2-dimethyl-oxazolidine-3-carboxylic acid tert.-butyl ester (3)

34.5 ml of a 1.6 molar solution of butyllithium in hexane are added at 0° to a solution of 5.25 g of diisopropylamine in 200 ml of dry tetrahydrofuran. The mixture is cooled to −75° C. and a solution of 15 g of acetate 2 according to b) in 100 ml of tetrahydrofuran is added dropwise within a period of 10 minutes, and after 5 minutes a solution of 8 g of tert.-butyldimethylsilyl chloride in 30 ml of 1,3-dimethyl-3,4,5,6-tetrahydro-2-(1H)-pyrimidinone is added. The mixture is allowed to warm up to room temperature and is then heated under reflux for 2 hours and cooled to room temperature. 230 ml of 45% ammonium fluoride solution are added, and the whole is stirred at room temperature for 20 hours and is then concentrated by evaporation. 150 ml of 1N sodium hydroxide solution are added, while cooling with ice, to the oily residue which is obtained after concentration of the organic phase by evaporation, and the mixture is extracted twice with 200 ml of dichloromethane each time. The aqueous phase is acidified with 300 ml of 20% citric acid solution and is extracted three times with 300 ml of dichloromethane each time. The organic phases are washed with 20% sodium chloride solution, dried over sodium sulphate and concentrated by evaporation. Chromatography of the residue on 50 g of silica gel using hexane/ethyl acetate 1:1 as eluant yields 11 g of solid 3.

d) (4R)-4-(4'-carbaethoxy-2'-methylbutenyl)-2,2-dimethyloxazolidine-3-carboxylic acid tert.-butyl ester (4)

d,a) Starting from the acid 3

3.9 ml of 1-amino-1-chloro-N,N,2-trimethylpropene are added dropwise within a period of 10 minutes to an ice-cooled solution of 7.8 g of carboxylic acid 3 according to c) in 100 ml of dry dichloromethane. After 30 minutes at 0°, a solution of 2.2 g of pyridine in 80 ml of ethanol is added within a period of 20 minutes. After stirring at room temperature for 12 hours, the mixture is diluted with 100 ml of dichloromethane and washed twice with 100 ml of water each time. The organic phase is dried over sodium sulphate and concentrated by evaporation. Chromatography of the residue on silica gel using hexane/ethyl acetate 10:1 yields 6.5 g of ester 4, $[\alpha]_D = +6.17°$ (c=1, CHCl$_3$). C$_{18}$H$_{31}$NO$_5$, calculated: C 63.32%, H 9.15%, N 4.10%; found: C 63.4%, H 9.2%, N 4.5%.

d,b) Starting from the epimer mixture 1

A solution of 8 g of alcohol 1 according to a) and 0.05 ml of propionic acid in 10.5 ml of orthoacetic acid triethyl ester is heated at 135°–140° for 14 hours, with ethanol slowly being distilled off. The whole is concentrated by evaporation at 40° under a high vacuum. Chromatography of the residue on silica gel using hexane/ethyl acetate 10:1 yields 8 g of 4.

e) (4R)-2,2-dimethyl-4-(5'-hydroxy-2'-methylpent-1'-enyl)oxazolidine-3-carboxylic acid tert.-butyl ester (5)

1.61 g of lithium aluminium hydride are added in portions at 0° to a solution of 14.5 g of 4 according to d) in 250 ml of absolute diethyl ether. The mixture is stirred at 0°–2° for 18 hours, and a solution of 5 g of potassium hydrogen sulphate in 60 ml of water is added while cooling with acetone/dry ice. The mixture is filtered and washed four times with 200 ml of diethyl ether each time. The organic phase is washed three times with 80 ml of 1N hydrochloric acid each time, three times with 80 ml of saturated sodium bicarbonate solution each time, and twice with 200 ml of saturated sodium chloride solution each time, and is then dried over sodium sulphate and concentrated by evaporation. Chromatography on silica gel using hexane/ethyl acetate 1:1 yields 11.3 g of 5, C$_{16}$H$_{29}$NO$_4$, calculated: C 64.19%, H 9.77%, N 4.68%; found: C 63.6%, H 9.8%, N 4.7%.

f) (4R)-4-(5'-bromo-2'-methylpent-1'-enyl)-2,2-dimethyloxazolidine-3-carboxylic acid tert.-butyl ester (6)

4.87 g of tetrabromomethane, 3.85 g of triphenylphosphine and 0.6 ml of pyridine are added at 0°–2° to a solution of 4.4 g of alcohol 5 according to e) in 200 ml of dichloromethane. After 12 hours at 0°–2°, a further 1 g of tetrabromomethane and 1 g of triphenylphosphine are added and the mixture is stirred at 0° for 6 hours. The mixture is concentrated by evaporation, taken up in ethyl acetate, filtered and concentrated. Chromatography on silica gel using hexane/ethyl acetate 10:1 yields 4.5 g of 6, C$_{16}$H$_{28}$NO$_3$Br; calculated: C 53.04%, H 7.79%, N 3.87%, Br 22.06%; found: C 53.1%, H 7.7%, N 3.9%, Br 21.6%.

g) (4R)-2,2-dimethyl-4-(2'-methyl-5'-diisopropyl-phosphonopent-1'-enyl)-oxazolidine-3-carboxylic acid tert.-butyl ester (7)

A solution of 10.9 g of bromide 6 in 22 ml of triisopropyl phosphite is heated at 135°–140° for 24 hours at 100 mbar. The excess reagent is evaporated off at 0.1 mbar/60°. Chromatography of the residue on silica gel using hexane/ethyl acetate 1:1 yields 10.7 g of 7.

h) N-((2R)-1-hydroxy-4-methyl-7-diisopropylphosphonohept-3-en-2-yl)-carbamic acid tert.-butyl ester (8)

3 g of Amberlyst® 15 (H$^+$ form) are added to a solution of 3 g of 7 according to g) in 100 ml of ethanol. The mixture is stirred at room temperature for 20 hours, filtered, concentrated by evaporation and chromatographed on 50 g of silica gel. Elution with ethyl acetate/methanol 10:1 yields 2.3 g of 8, $[\alpha]_D = -5.9°$ (c=1, CHCl$_3$). C$_{19}$H$_{38}$NO$_6$P; calculated: C 56.0%, H 9.4%, N 3.44%, P 7.6%; found: C 55.4%, H 9.3%, N 3.4%, P 7.3%.

i) (2R)-2-tert.-butoxycarbonylamino-4-methyl-7-diisopropylphosphono-3-heptenoic acid (9)

i,a) Oxidation with chromic acid 0.84 ml of a solution which is 3.25 molar in chromium trioxide and 5.29 molar in sulphuric acid is added dropwise at 0°–5° to a solution of 0.5 g of alcohol 8 according to h) in 15 ml of acetone. The mixture is stirred at 0° for 30 minutes and at room temperature for 35 minutes, and then 4 ml of isopropanol, 80 ml of ethyl acetate and 30 ml of 20% sodium chloride solution are added thereto, and the mixture is filtered. The aqueous phase is extracted three times with 20 ml of ethyl acetate each time. The organic phase is dried over sodium sulphate and concentrated by evaporation. Chromatography on 20 g of silica gel using hexane/ethyl acetate/acetic acid 16:10:1 yields 0.34 g of 9, $[\alpha]_D = -35.25°$ (c=1.39, CHCl$_3$), −C-NMR (75 MHz, CDCl$_3$): 173.8 (CO$_2$H); 155.0 (OCON); 140.4 (C(4)); 121.1 (C(3)); 79.5 (OC(CH$_3$)$_3$); 70.3 (OCH); 52.1 (C(2)); 39.7 (d, J=18, C(5)); 28.3 ((CH$_3$)$_3$C); 25.7 (d, J=142, C(7)); 24.0 ((CH$_3$)$_2$CH); 20.2 (d, J=5, C(6)).

i,b) Oxidation with platinum/oxygen

To a solution of 3 g of alcohol 8 according to h) in 105 ml of dioxan there is added at 55° a suspension of platinum in 45 ml of water prepared by hydrogenation and degassing of 1 g of platinum oxide in 45 ml of water. Oxygen is passed through the mixture at 55°–60° with vigorous stirring (approximately 1900 rpm). The mixture is filtered through Celite ® and washed twice with 80 ml of water each time, and the filtrate is concentrated by evaporation at 40° under a high vacuum. The resulting product is dissolved in 200 ml of water, and 1 g of sodium bicarbonate and 50 ml of 20% sodium chloride solution are added and the mixture is extracted three times with 100 ml of ethyl acetate each time. The organic phases are dried over sodium sulphate. Filtration and concentration by evaporation yield 1.8 g of educt 8. The aqueous phase is acidified with approximately 20 ml of 1N sulphuric acid and extracted five times with 120 ml of ethyl acetate each time. Drying over sodium sulphate, concentration by evaporation and chromatography of the residue according to i,a) yield 0.8 g of acid 9.

j) (2R)-2-amino-4-methyl-7-phosphono-3-heptenoic acid (10)

A solution of 3.3 g of acid 9 according to i) and 2.6 g of N,O-bis-trimethylsilylacetamide is stirred at room temperature for one hour under argon. After the addition of 4.4 g of trimethylbromosilane, the mixture is stirred for 24 hours. The reaction mixture is added dropwise at 0° to 400 ml of water, and the whole is stirred for 30 minutes. The organic phase is separated off and washed three times with 50 ml of water each time. The aqueous phases are extracted three times with 30 ml of dichloromethane each time and concentrated to 10 ml at 40° under a high vacuum. Chromatography on 20 ml of Dowex ® 50 W×8 using water as eluant, and lyophilisation of the eluate yield 0.4 g of 10 in the form of an amorphous white powder having a melting point of 252° (decomposition); $[\alpha]_D = -86.5°$ (c=1, H$_2$O); C$_8$H$_{16}$NO$_5$P.1 H$_2$O; calculated: C 37.05%, H 6.9%, N 5.5%; found: C 36.3%, H 6.5%, N 5.6%.

In order to analyse the purity of the enantiomer, a sample is derivatised to the amide with (R)-(+)-methoxytrifluoromethylphenylacetic acid chloride. $^1$H-NMR analysis (300 MHz) by integration of the OCH$_3$ signals gives ≧94% (2R)-isomer (3.24 ppm) and ≦6% (2S)-isomer (3.17 ppm).

EXAMPLE 30

(2R)-2-amino-7-phosphono-3-heptenoic acid a) (4R)-2,2-dimethyl-4-(1'-hydroxyprop-2'-enyl)-oxazolidine-3-carboxylic acid tert.-butyl ester (1)

60 ml of a 2.4M solution of vinylmagnesium bromide in tetrahydrofuran are added at 0°–5° within a period of 30 minutes to a solution of 25 g of (4S)-2,2-dimethyl-4-formyloxazolidine-3-carboxylic acid tert.-butyl ester (according to Example 43c) in 300 ml of dry tetrahydrofuran. The mixture is stirred at 0° for one hour, allowed to warm up to room temperature and then stirred at room temperature for a further one hour. 300 ml of buffer solution (1 molar, phosphate, pH 7) are added while cooling to 10°. After 10 minutes, the mixture is filtered, extracted twice with 150 ml of ethyl acetate each time and washed twice with 100 ml of water each time. The aqueous phase is extracted twice with 100 ml of ethyl acetate each time. The organic extracts are dried over sodium sulphate and concentrated by evaporation. Chromatography of the residue on silica gel using hexane/ ethyl acetate 4:1 yields 24.2 g of epimer mixture 1; C$_{13}$H$_{23}$NO$_4$; calculated: C 60.68%, H 9.01%, N 5.44%; found: C 60.7%, H 9.1%, N 5.6%.

b) (4R)-4-(4'-ethoxycarbonylbutenyl)-2,2-dimethyloxazolidine-3-carboxylic acid tert.-butyl ester (2)

A solution of 22.5 g of alcohol 1 according to a) and 0.3 ml of propionic acid in 38.5 ml of orthoformic acid triethyl ester is heated at 135°–140° C. for 4 hours, with ethanol slowly being distilled off. The mixture is concentrated by evaporation at 50° under a high vacuum and chromatographed on 300 g of silica gel. Elution with hexane/ethyl acetate 4:1 yields 23.9 g of 2, $[\alpha]_D = -10.0°$ (c=1.5, CHCl$_3$); C$_{17}$H$_{29}$NO$_5$; calculated: C 62.36%, H 8.93%, N 4.28%; found: C 62.2%, H 8.9%, N 4.4%.

c) (4R)-2,2-dimethyl-4-(5'-hydroxypentenyl)-oxazolidine-3-carboxylic acid tert.-butyl ester (3)

2.7 g of lithium aluminium hydride are added in portions at 0°–2° to a solution of 23.5 g of 2 according to b) in 550 ml of absolute diethyl ether. After stirring at 0°–2° for 3 hours, a solution of 25 g of potassium hydrogen sulphate in 250 ml of water is added dropwise with cooling. The mixture is filtered through Celite ® and washed thoroughly with diethyl ether. The organic phase is washed twice with 200 ml of 1N hydrochloric acid each time and twice with 250 ml of 10% sodium bicarbonate solution each time. The aqueous phases are extracted twice with 100 ml of ether each time. The organic phases are washed with 20% sodium chloride solution, dried over sodium sulphate and concentrated by evaporation. Chromatography on silica gel using hexane/ethyl acetate as eluant yields 18.6 g of 3, $[\alpha]_D = -10.1°$ (c=1.4, CHCl$_3$); C$_{15}$H$_{27}$NO$_4$; calculated: 63.13%, H 9.54%, N 4.91%; found: C 63.0%, H 9.5%, N 5.0%.

d) (4R)-4-(5'-bromopentenyl)-2,2-dimethyloxazolidine-3-carboxylic acid tert.-butyl ester (4)

7 ml of pyridine are added dropwise at 0° to a solution of 18.5 g of alcohol 3 according to c), 28.2 g of tetrabromomethane and 22.3 g of triphenylphosphine in 600 ml of dichloromethane. The mixture is stirred at 0°–2° for 12 hours, concentrated by evaporation, taken up in 150 ml of ethyl acetate, filtered, concentrated to 50 ml and chromatographed on 200 g of silica gel. Elution with hexane/ethyl acetate 10:1 yields 19.9 g of bromide 4, $[\alpha]_D = -18.9°$ (c=1, CHCl$_3$); C$_{15}$H$_{26}$NO$_3$Br; calculated: C 51.73%, H 7.53%, N 4.02%, Br 22.94%; found: C 51.7%, H 7.7%, N 4.2%, Br 23.0%.

e) (4R)-2,2-dimethyl-4-(5'-di-2-propylphosphonopentenyl)oxazolidine-3-carboxylic acid tert.-butyl ester (5)

A solution of 19.9 g of bromide 4 according to d) in 60 ml of triisopropyl phosphite is heated at 130°–135° for 20 hours at 100 mbar. The excess reagent is distilled off at 60°/0.1 mbar, and the residue is chromatographed on 250 g of silica gel. Elution with hexane/ethyl acetate 1:1 yields 20.6 g of phosphonic acid ester 5, $[\alpha]_D = -8.6°$ (c=0.8, CHCl$_3$); C$_{21}$H$_{40}$NO$_6$P; calculated: C 58.18%, H 9.30%, N 3.23%, P 7.15%; found: C 57.4%, H 9.3%, N 3.2%, P 7.5%.

f) N-((2R)-1-hydroxy-7-(diisopropylphosphonohept-3-en-2-yl)carbamic acid tert.-butyl ester (6)

A solution of 20.6 g of 5 according to e) in 800 ml of methanol is stirred at room temperature for 20 hours with 30 g of Amberlyst ® 15 (H+ form). The mixture is filtered, washed with methanol, concentrated by evaporation and chromatographed on 100 g of silica gel. Elution with ethyl acetate yields 14.8 g of 6, $[\alpha]_D = -3.6°$ (c=1.5, CHCl$_3$); C$_{18}$H$_{36}$NO$_6$P; calculated: C 54.95%, H 9.22%, N 3.56%, P 7.87%; found: C 53.6%, H 9.0%, N 3.4%, P 9.0%.

g) (2R)-2-tert.-butoxycarbonylamino-7-diisopropylphosphono-3-heptenoic acid (7)

To a solution of 7.4 g of alcohol 6 according to f) in 300 ml of acetone there are added dropwise at 0°–2° C., within a period of 20 minutes, 15 ml of a solution which is 3.25 molar in chromium trioxide and 5.29 molar in sulphuric acid. The mixture is stirred at 0°–2° for 2 hours and at room temperature for 4 hours, and then 30 ml of isopropanol, 300 ml of ethyl acetate and 200 ml of 20% sodium chloride solution are added. The aqueous phase is extracted three times with 250 ml of ethyl acetate each time, and the organic phases are dried over sodium sulphate and concentrated by evaporation. Chromatography on 200 g of silica gel using hexane/ethyl acetate/acetic acid 16:10:1 yields 4.55 g of acid 7, $[\alpha]_D = -24.9°$ (c=0.8, CHCl$_3$).

h) (2R)-2-amino-7-phosphono-3-heptenoic acid (8)

A solution of 3.1 g of acid 7 and 3 ml of N,O-bis-trimethylsilylacetamide in 200 ml of dry dichloromethane is stirred at room temperature for one hour. 3.5 ml of trimethylbromosilane are added, and the mixture is stirred at room temperature for 30 hours. The volatile portions are evaporated off, the residue is taken up in 50 ml of dichloromethane, and 250 ml of water are added at 0°–2°. The aqueous phase is separated off and concentrated to 10 ml under a high vacuum. Chromatography on 20 ml of Dowex ® 50 W×8 using water as eluant, and lyophilisation of the eluate yield 1.04 g of 8 in the form of an amorphous powder, $[\alpha]_D = -65.2°$ (c=1, H$_2$O); $^{13}$C-NMR (75 MHz, D$_2$O): 172.8 (CO$_2$H); 140.3 (C(4)); 122.2 (C(3)); 56.4 (C(2)); 33.3 (d, J=17, C(5)); 27.3 (d, J=134, C(7)); 22.6 (d, J=4, C(6)). In order to analyse the purity of the enantiomer, a sample is derivatised to the amide trimethyl ester with (R)-(+)-methoxytrifluoromethylphenylacetic acid chloride followed by diazomethane. $^1$H-NMR analysis (300 MHz) by integration of the OCH$_3$ signals gives ≧95% (2R)-isomer (3.54 ppm) and ≦5% (2S)-isomer (3.37 ppm).

EXAMPLE 31

(2R)-2-amino-4-methyl-5-phosphono-3-pentenoic acid ethyl ester a) (2R,3S)-2-formylamino-3-hydroxy-4-methyl-4-pentenoic acid ethyl ester (1)

aa) Starting from 1,1,3,3-tetramethyl-1,3-disila-2-azolidine-N-acetic acid ethyl ester 7.6 ml of a 1.6 molar solution of butyllithium in hexane are added at −20° to a solution of 2.26 ml of N-cyclohexyl-N-isopropylamine in 60 ml of absolute tetrahydrofuran. After 20 minutes, the mixture is cooled to −78° and there is added dropwise a solution of 3 g of 1,1,3,3-tetramethyl-1,3-disila-2-azolidine-N-acetic acid ethyl ester in 60 ml of tetrahydrofuran. The mixture is stirred at −78° for one hour, and then 142 ml of an approximately 0.035 molar solution of cyclopentadienyl-bis-1,2:5,6-di-O-isopropylidene-D-glucofuranosyl-titanium(IV) chloride in ether are added and the mixture is stirred at −78° for 17 hours. The reaction solution is transferred via a small steel tube, by argon pressure, into a vessel containing a solution, cooled to −78°, of 1.1 ml of methacrolein in 15 ml of tetrahydrofuran. The whole is allowed to warm up slowly to room temperature, and is then stirred for 2 hours. 1.5 ml of water are added, and the mixture is filtered. The filtrate is diluted with 250 ml of diethyl ether, and is then washed three times with 250 ml of approximately 10% sodium chloride solution each time and with 250 ml of saturated sodium chloride solution. The aqueous phases are extracted twice with 250 ml of diethyl ether each time. The organic phases are dried over sodium sulphate, concentrated by evaporation, and dissolved hot in 150 ml of cyclohexane. On cooling, 1,2:5,6-di-O-isopropylidene-D-glucofuranose crystallises. The mother liquor is concentrated by evaporation, the residue is taken up in 120 ml of tetrahydrofuran, 24 ml of water and 4.5 ml of acetic acid, and the mixture is stirred at room temperature for 2 hours. Concentration by evaporation at room temperature under a high vacuum yields 10.6 g of residue, contamining (2R,3S)-2-amino-3-hydroxy-4-methyl-4-pentenoic acid ethyl ester. A sample (5 mg) is derivatised for 2 hours with 0.2 ml of trifluoroacetic acid anhydride in 0.3 ml of dichloromethane. Capillary gas chromatography (Chirasil ®-L-Val, 90°–180°/2° per minute) yields 99.25% (2R,3S)-enantiomer (retention time T$_{ret}$=10.28 minutes) and 0.75% (2S,3R)-enantiomer (retention time T$_{ret}$=11.48 minutes). The main mixture is then heated under reflux for 5½ hours in 80 ml of formic acid ethyl ester. Concentration by evaporation and chromatography on silica gel using hexane/ethyl acetate 1:1 yield 1.64 g of formamide 1. Analysis of a sample (5 mg) in the form of the acetate by gas chromatography (Chirasil ®-L-Val, 160°–180°, 1° per minute): 99.2% (2R,3S)-enantiomer (T$_{ret}$=13.64 minutes), 0.8% (2S,3R)-enantiomer (T$_{ret}$=13.94 minutes).

a,b) Starting from isocyanoacetic acid ethyl ester 1.65 g of (S)-N-methyl-N-[2-(dimethylamino)-ethyl]-1-[(R)1',2-bis-(diphenylphosphino)-ferrocenyl]-ethylamine and 1.105 g of bis(cyclohexylisocyanide)gold(I) tetrafluoroborate are added at 50° to a solution of 24.88 g of isocyanoacetic acid ethyl ester and 18.51 g of methacrolein in 220 ml of 1,2-dichloromethane. The mixture is stirred at 50° for 5 hours under argon, concentrated by evaporation, taken up in 400 ml of diethyl ether and filtered, and the filtrate is concentrated by evaporation. Distillation of the residue under a high vacuum (0.04 mbar) yields 33.62 g of a stereoisomeric mixture of 5-(2-propenyl)-oxazoline-4-carboxylic acid ethyl ester having a boiling point of 42°–52°; MS.: m/e = 183 (2%, M+), 110 (80%), 85 (100%). A solution of 33 g of this mixture in 74 ml of water and 33 ml of tetrahydrofuran is heated under reflux for 3 hours. Concentration by evaporation in vacuo yields 36.1 g of a mixture of stereo-isomeric 2-formamino-3-hydroxy-4-methyl-4-pentenoic acid ethyl ester 2. A sample (35 mg) is derivatised in 2 ml of dichloromethane with 0.05 ml of N,O-bis-trimethylsilylacetamide and analysed by means of capillary gas chromatography (Chirasil ®-L-Val, 150°): 89.1% (2R,3S)-isomer (T$_{ret}$=22.1 minutes), 5.8% (2S,3R)-isomer (T$_{ret}$=23.1 minutes), 2.8% (2R,3R)-isomer (T$_{ret}$=24.3 minutes), 2.3% (2S,3S)-isomer (T$_{ret}$=25.4 minutes).

A solution of 11.42 ml of acetic anhydride in 50 ml of dichloromethane is added dropwise at 0°–3° within a period of 25 minutes to a solution of 20.2 g of 2, 16.83 ml of triethylamine and 0.62 g of 4-(dimethylamino)-pyridine in 300 ml of dichloromethane. After 30 minutes, the mixture is washed twice with ice-cold 2N hydrochloric acid and twice with 10% sodium chloride solution. The aqueous phases are extracted with 100 ml of dichloromethane. The organic phases are dried over sodium sulphate and concentrated by evaporation, and the residue is dissolved hot in hexane/ ethyl acetate 4:1. On cooling slowly to approximately 30° there crystallise 1.82 g of racemic (2R*,2S*)-2-formamino-3-acetoxy-4-methyl-4-pentenoic acid ethyl ester having a melting point of 98°–106°. The mother liquor is slowly cooled to −12° C. and kept at that temperature for one hour. Filtration yields 15.04 g of acetate 3, m.p. 73°–75°, $[\alpha]_D = -75.6°$ (c=1, CHCl$_3$), analysis by gas chromatography (Chirasil ®-L-Val, 160°–180°, 1° per minute): (2R,3S)-isomer 93.5% ($T_{ret}$=14.5 minutes), (2S,3R)-isomer 2.2% ($T_{ret}$=14.8 minutes), (2R,3R)-isomer 2.2% ($T_{ret}$=16.8 minutes), (2S,3S)-isomer 2.1% ($T_{ret}$=17.1 minutes). 20.64 g of anhydrous potassium carbonate are added at −16° to a solution of (2R,3S)-2-formylamino-3-acetoxy-4-methyl-4-pentenoic acid ethyl ester (3) in 400 ml of absolute ethanol. After stirring at −18° to −11° C. for 4 hours, 500 ml of buffer solution (1 molar, phosphate, pH=7) are added dropwise. The mixture is stirred at room temperature for 30 minutes and extracted three times with 350 ml of dichloromethane each time. The organic phases are dried over sodium sulphate and concentrated by evaporation, and the residue is chromatographed on 1 kg of silica gel using hexane/ethyl acetate 1:2 as eluant, yielding 9.8 g of alcohol 1.

b) (2R)-2-formylamino-4-methyl-5-diisopropylphosphono-3-pentenoic acid ethyl ester (4)

To a solution of 14.19 g of 1 according to a) in 210 ml of 1,2-dichloroethane there are added at 18°–20° 6.57 ml of thionyl bromide and, after stirring for 2 hours, 135 ml of water. After 15 minutes, the organic phase is separated off and washed three times with 150 ml of ice-water each time and once with 100 ml of ice-cooled saturated sodium hydrogen carbonate solution. The organic phase is dried over sodium sulphate and concentrated by evaporation, and the residue is dissolved in 60 ml of triisopropyl phosphite and stirred at 75°/100 mbar for 17 hours. The excess reagent is distilled off at 90° under a high vacuum. Chromatography of the residue on 650 g of silica gel using ethyl acetate/methanol 20:1 yields 10.88 g of phosphonic acid ester 4, $[\alpha]_D = -123.5°$ (c=1, CHCl$_3$). $^1$H-NMR analysis (300 MHz) with the addition of (1R)-1-(9′-anthracenyl)-2,2,2-trifluoroethanol shows an enantiomeric purity of ≥90%.

c) (2R)-2-amino-4-methyl-5-phosphono-3-pentenoic acid ethyl ester (5)

23 ml of trimethylbromosilane are added dropwise at room temperature within a period of 15 minutes to a solution of 10.3 g of 4 according to b) in 42 ml of dichloromethane. After 21½ hours, 42 ml of ethanol are added while cooling with ice, and the mixture is stirred for 20 hours. The whole is then concentrated by evaporation and the residue is dissolved three times in 70 ml of toluene each time and in each case is concentrated by evaporation again. The residue is dissolved in 42 ml of ethanol, and 42 ml of propylene oxide are added. After 1½ hours, the mixture is filtered. Drying the filtration residue in a vacuum desiccator over P$_2$O$_5$/KOH (3 hours/80°) yields 6.17 g of 5; $[\alpha]_D = -78°$ (c=0.6, H$_2$O); m.p. 194°–197° (decomp.), C$_8$H$_{16}$NO$_5$P; calculated: C 40.51%, H 6.80%, N 5.91%, P 13.06%; found: C 39.4%, H 7.09%, N 5.73%, P 12.98%.

In order to analyse the purity of the enantiomer, a sample is derivatised to the amide dimethyl phosphonate with (R)-(+)-methoxytrifluoromethylphenylacetic acid chloride and diazomethane and analysed by $^1$H-NMR (300 MHz) using the integration of the OCH$_3$ signals: (2R)-isomer ≥93% (3.51 ppm), (2S)-isomer ≤7% (3.37 ppm).

EXAMPLE 32

(2R)-2-E-amino-4methyl-5-phosohono-3-pentenoic acid

A solution of 100 mg of (2R)-2-amino-4-methyl-5-phosphono-3-pentenoic acid ethyl ester according to Example 28 in 3 ml of 1N hydrochloric acid is heated in a bath at 100° C. for 4½ hours. The solution is concentrated by evaporation and the residue is dried at 60° under a high vacuum for 30 minutes. The residue is dissolved in 15 ml of ethanol, and 4 ml of propylene oxide are added thereto. Filtration and drying of the filtration residue in a vacuum desiccator over P$_2$O$_5$/KOH yield 62 mg of acid.

In order to determine the purity of the enantiomer, a sample is derivatised to the amide with (R)-(+)-methoxytrifluoromethylphenyl acetic acid chloride and is analysed by 1H-NMR (300 MHz), integration of the OCH$_3$signals: ≥95% (2R)-enantiomer (3.25 ppm) and ≤5% (2S)-enantiomer (3.18 ppm).

EXAMPLE 33

E-2-amino-4-methyl-5-phosphono-3-pentenoic acid 12 g of E-2-amino-4-methyl-5-phosphono-3-pentenoic acid ethyl ester are stirred under reflux in 70 ml of water for 19 hours. The reaction mixture is slowly cooled to room temperature, stirred in an ice bath for one hour, filtered and washed with cold water. In this manner there is obtained E-2-amino-4-methyl-5-phosphono-3-pentenoic acid in the form of the monohydrate, m.p. 163° (decomp.).

EXAMPLE 34

E-2-dimethylamino-4-methyl-5-phosphono-3-pentenoic acid

A mixture of 3.56 g of E-2-amino-4-methyl-5-phosphono-3-pentenoic acid ethyl ester, 45 ml of 98% formic acid and 30 ml of 37% aqueous formaldehyde solution is stirred at a bath temperature of 105° for 30 minutes. The mixture is then concentrated to dryness by evaporation in vacuo. The residue is taken up in a little water and the whole is again concentrated by evaporation in vacuo. This procedure is repeated twice more. The solid residue is stirred with 80 ml of water. After one hour, the undissolved material is separated off over a hard filter and washed with water. The filtrate and the washing water are concentrated to dryness by evaporation in vacuo. The residue is suspended in 100 ml of water and, after the addition of 30 ml of 1N sodium hydroxide solution, is left to stand at room temperature for 2 days. The reaction mixture is concentrated to a residual volume of approximately 25 ml by evaporation in vacuo and purified by ion exchanger chromatography (Dowex 50 W×8 H$_2$O). The fractions which contain the desired product are combined, concentrated by evaporation in vacuo and recrystallised from water/ethanol. In this manner there is obtained E-2-dimethylamino-4-methyl-5-phosphono-3-pentenoic acid, m.p. 239° (decomp.).

EXAMPLE 35

E-2-dimethylamino-4-methyl-5-phosphono-3-pentenoic acid ethyl ester 30 ml of 8N ethanolic hydrogen chloride solution are added to 1.19 g of E-2-dimethylamino-4-methyl-5-phosphono-3-pentenoic acid, and the mixture is stirred at 40° for 24 hours. The reaction mixture is concentrated to dryness by evaporation in vacuo. After the addition of 30 ml of pure ethanol, the mixture is again concentrated by evaporation, giving 1.90 g of reddish oil, which is dissolved in hot isopropanol. After cooling there is obtained crystalline E-2-dimethylamino-4-methyl-5-phosphono-3-pentenoic acid ethyl ester hydrochloride, m.p. 203° (decomp.).

EXAMPLE 36

E-2-benzylamino-4-methyl-5-phosphono-3-pentenoic acid ethyl ester 16 ml of glacial acetic acid, 5.90 g of sodium acetate (anhydrous) and 12.2 ml of benzaldehyde are added to a solution of 5.69 g of E-2-amino-4-methyl-5-phosphono-3-pentenoic acid ethyl ester in 48 ml of water and 48 ml of ethanol. 15.70 g of sodium borohydride are added in approximately 70 portions within a period of one hour with intensive cooling with ice/sodium chloride, 4 ml of benzaldehyde being added after half the addition has taken place, after approximately 30 minutes. The temperature of the reaction mixture is kept at from 0° to 10°. When the addition is complete, the mixture is stirred at 0° for one hour to complete the reaction, and then 1N hydrochloric acid is added dropwise until an acidic reaction to Congo red takes place. The undissolved salts are filtered off and washed with water. The filtrate is concentrated to dryness by evaporation in vacuo, and the residue is concentrated by evaporation twice more after the addition of ethanol. The residue is then stirred with 150 ml of ethanol, and the undissolved material is filtered off with suction and washed with ethanol. 25 ml of propylene oxide are added to the filtrate, and the mixture is then stirred for 2 hours. The material which crystallises out (mainly educt) is filtered off. The mother liquor is concentrated to dryness by evaporation and stirred with 350 ml of ethyl acetate. The crystalline crude product obtained after filtration with suction is recrystallised from ethanol. In this manner there is obtained E-2-benzylamino-4-methyl-5-phosphono-3-pentenoic acid ethyl ester, m.p. 192° (decomp.).

EXAMPLE 37

E-2-benzylamino-4-methyl-5-phosphono-3-pentenoic acid ethyl ester

A solution of 1.00 g of E-2-benzylamino-4-methyl-5-phosphono-3-pentenoic acid ethyl ester in 6 ml of water is stirred under reflux for 20 hours. The reaction mixture is concentrated to dryness by evaporation in vacuo. Ethanol is added to the residue, and the mixture is again concentrated by evaporation. This process is repeated twice more. The residue is dissolved in boiling methanol. After cooling there is obtained crystalline E-2-benzylamino-4-methyl-5-phosphono-3-pentenoic acid, m.p. 150° (decomp.).

EXAMPLE 38

E-2-isopropylamino-4-methyl-5-phosphono-3-pentenoic acid ethyl ester 6.64 g of sodium acetate (anhydrous) and 18 ml of acetone are added to a solution of 6.40 g of E-2-amino-4-methyl-5-phosphono-3-pentenoic acid ethyl ester in 54 ml of water and 18 ml of glacial acetic acid. 17.67 g of sodium borohydride are added in approximately 70 portions within a period of 90 minutes with intensive cooling with ice/sodium chloride, 18 ml of acetone being added after 20 minutes and after 50 minutes. When the addition is complete, the thick white suspension is stirred at 0° for 30 minutes to complete the reaction, and then 1N hydrochloric acid is added dropwise until an acidic reaction to Congo red takes place. The resulting clear solution is concentrated by evaporation in vacuo, and the residue is concentrated by evaporation twice more after the addition of ethanol. The residue is then stirred with 200 ml of ethanol at room temperature, and the undissolved material is filtered off and washed with ethanol. The filtrate is concentrated by evaporation in vacuo, and the residue is recrystallised from isopropanol.

In this manner there is obtained E-2-isopropylamino-4-methyl-5-phosphono-3-pentenoic acid ethyl ester hydrochloride, m.p. 203°-205° (decomp.).

EXAMPLE 39

E-2-isopropylamino-4-methyl-5-phosphono-3-pentenoic acid

A solution of 1.20 g of E-2-isopropylamino-4-methyl-5-phosphono-3-pentenoic acid ethyl ester hydrochloride in 7 ml of water is stirred under reflux for 20 hours. The reaction mixture is concentrated to dryness by evaporation in vacuo. Ethanol is added to the residue, and the mixture is again concentrated by evaporation. This process is repeated twice more. The residue is dissolved in 25 ml of ethanol, a total of 5 ml of propylene oxide is added dropwise thereto with stirring, and the whole is concentrated to dryness by evaporation. The residue is dissolved in a little water, and ethanol is added until the solution becomes cloudy. The solution is stirred at room temperature for 4 hours to complete the reaction, during which time crystallisation slowly takes place. The product is filtered off, washed with ethanol and diethyl ether and dried at 100° under a high vacuum. In this manner there is obtained E-2-isopropylamino-4-methyl-5-phosphono-3-pentenoic acid, m.p. 225°-227° (decomp.).

EXAMPLE 40

E-2-methylamino-4-methyl-5-phosphono-3-pentenoic acid a) 2-(N-methyl-N-formylamino)-3-hydroxy-4-methyl-4-pentenoic acid ethyl ester (1)

20.60 g of 5-(2-propenyl)-2-oxazoline-4-carboxylic acid ethyl ester, prepared according to Example 55, are dissolved in 200 ml of dry dichloromethane under argon. A suspension of 16.60 g of trimethyloxonium tetrafluoroborate in 200 ml of dry dichloromethane is then added dropwise at 15°. The reaction mixture is stirred at room temperature for 17 hours, and then 150 ml of water and 45 ml of saturated potassium bicarbonate solution are added slowly, so that a pH of 7 is produced. The organic phase is separated off and washed twice with water and once with saturated sodium chloride solution, and is then dried over sodium sulphate. After the dichloromethane has been distilled off, the oily residue is distilled in a bulb tube, b.p. 120°–130°/13 Pa. In this manner there is obtained 2-(N-methylformylamino)-3-hydroxy-4-methyl-4-pentenoic acid ethyl ester in the form of a light-yellow honey, IR (CH$_2$Cl$_2$): 3550 (HO); 1740 (CO ester); 1675 (CO amide).

b) E-2-(N-methyl-N-formylamino)-4-methyl-5-diisopropylphosphono-3-pentenoic acid ethyl ester (2)

7.70 ml of thionyl bromide are added dropwise at 20° under argon to a solution of 17.80 g of 2-(N-methylformylamino)-3-hydroxy-4-methyl-4-pentenoic acid ethyl ester in 248 ml of 1,2-dichloroethane. The mixture is stirred at room temperature for 2 hours. 150 ml of water are then added dropwise with slight cooling (20°). The two-phase mixture is stirred thoroughly for a further 20 minutes to complete the reaction. The organic phase is separated off and washed three times with water/ice, once with ice/saturated potassium bicarbonate solution and once with saturated sodium chloride solution. To the intermediate obtained after drying over sodium sulphate and removal of the 1,2-dichloroethane by distillation at 35° in vacuo there are added at room temperature 66 ml of triisopropyl phosphite, and the mixture is then stirred at 75° under reduced pressure (approximately 13 kPa) for 17 hours. The excess triisopropyl phosphite and other volatile by-products are then distilled off under a high vacuum. Purification by column chromatography (silica gel, ethyl acetate) yields E-2-(N-methylformylamino)-4-methyl-5-diisopropylphosphono-3-pentenoic acid ethyl ester in the form of a yellowish honey; IR (CH$_2$Cl$_2$): 1740 (CO ester); 1670 (CO amide); 1235 (P=O); 980–1010 (P—O—C). According to the $^1$H-NMR spectrum, the compound is in the form of a mixture of two rotamers.

c) E-2-methylamino-4-methyl-5-phosphono-3-pentenoic acid (3) 20 ml of trimethylbromosilane are added dropwise at 20° within a period of 10 minutes under argon to a solution of 9.50 g of E-2-(N-methylformylamino)-4-methyl-5-diisopropylphosphono-3-pentenoic acid ethyl ester in 40 ml of dry dichloromethane. After stirring at room temperature for 20 hours, 37 ml of ethanol are added dropwise within a period of 15 minutes, and the whole is stirred for a further 20 hours. The clear reaction solution is then concentrated to dryness by evaporation in vacuo. The residue is concentrated by evaporation twice more in each case after the addition of 30 ml of toluene. 128 ml of 2N hydrochloric acid are added to the resulting oil, and the mixture is stirred at a bath temperature of 85° for 16 hours. The reaction mixture is concentrated by evaporation in vacuo. Concentration by evaporation twice after the addition of ethanol/toluene 1:1 yields an oily residue, which is dissolved in 51 ml of ethanol and to which there is added dropwise a solution of 51 ml of propylene oxide in 51 ml of ethanol. The product obtained in crystalline form is filtered off after 2 hours and recrystallised from water/ethanol. In this manner there is obtained E-2-methylamino-4-methyl-5-phosphono-3-pentenoic acid, m.p. 239° (decomp.).

EXAMPLE 41

23 ml (178 mmols) of trimethylsilyl bromide are added dropwise at room temperature to a solution of 18.3 g (44.5 mmols) of benzyl E-2-formylamino-4-methyl-5-diisopropylphosphono-3-pentenoate in 73 ml of dichloromethane. After 20 hours at room temperature 46 ml of benzyl alcohol are added dropwise, and the reaction mixture is allowed to stand for additional 20 hours at room temperature. The dichloromethane is distilled off, first 40 ml of ethanol and then dropwise 40 ml of propylene oxide in 40 ml of ethanol are added. The crystalline precipitate formed is filtered off, triturated with 200 ml of water and filtrated off again. Benzyl E-2-amino-4-methyl-5-phosphono-pentenoate of m.p. 196°–197° (decomp.) is thus obtained.

The starting material can be prepared as follows:

32.8 ml (65.6 mmols) of a 2N aqueous sodium hydroxide solution are added to a solution of ethyl E-2-formylamino-4-methyl-5-diisopropylphosphono-3-pentenoate in 230 ml of ethanol. After stirring for 1 hour at room temperature 32,8 ml (65,6 mmols) of 2N hydrochloric acid are added and the reaction mixture is evaporated to dryness. This procedure is repeated twice. Then the residue is dissolved in dichloromethane, filtrated over Hyflo ® and concentrated until crystallization begins. 200 ml of diethyl ether are added to complete crystallization. The resulting E-2-formylamino-4-methyl-5-diisopropylphosphono-pentenoic acid is filtrated off; m.p. 101°–106°.

11.5 g (56.4 mmols) of dicyclohexylcarbodiimid are added to a solution of 18.1 g (56.4 mmols) of E-2-formylamino-4-methyl-5-diisopropylphosphono-pentenoic acid, 6.1 g (56.4 mmols) of benzyl alcohol and 0.7 g of 4-(N,N-dimethylamino)pyridine in 140 ml of dichloromethane. The reaction mixture is stirred 2 hours in an ice bath and 10 hours at room temperature. The reaction solution is filtrated clear, washed with diluted hydrochloric acid and twice with water, dried over magnesium sulfate and chromatographed over silica gel with first ethyl acetate and then ethyl acetate/isopropanol as eluent. Benzyl E-2-formylamino-4-methyl-5-diisopropylphosphono-3-pentenoate is obtained as an orange-colored oil which can be crystallized from diethyl ether/hexane; m.p. 50°–58°.

EXAMPLE 42

A mixture of 2.37 g (10 mmols) of ethyl E-2-amino-4-methyl-5-phosphono-pentenoate, 14.3 g (100 mmols) of p-chlorobenzyl alcohol, 10 ml of dichloromethane and 20 ml of 4N hydrochloric acid is allowed to stand at room temperature for 1 week. The reaction mixture is evaporated to dryness, the residue is dissolved in 25 ml of ethanol and a solution of 15 ml of propylene oxide in 15 ml of ethanol is added dropwise. The crystalline precipitate formed is collected, washed twice with water, filtrated and dried. p-chlorobenzyl E-2-amino-4-methyl-5-phosphono-pentenoate of m.p. 207°–208° is thus obtained.

EXAMPLE 43

In an analogous manner as described in Examples 41 or 42, the following compounds can be prepared:
o-chlorobenzyl E-2-amino-4-methyl-5-phosphono-pentenoate, m.p. 216°–219° (decomp.);
p-fluorobenzyl E-2-amino-4-methyl-5-phosphono-pentenoate, m.p. 190°–191° (decomp.), and
m-chlorobenzyl E-2-amino-4-methyl-5-phosphono-pentenoate, m.p. 193° (decomp.).

EXAMPLE 44

In an analogous manner as described in anyone of Examples 1 to 40 also
2-E-amino-4-(p-chlorophenyl)-5-phosphono-3-pentenoic acid, m.p. 216° (decomp.), and (2R)-2-E-amino-4-fluoro-5-phosphono-3-pentenoic acid, m.p. 209° (decomp.)
can be manufactured.

EXAMPLE 45

Preparation of 1000 capsules each containing 10 mg of the active ingredient of Example 6 and having the following composition:

| E-2-amino-4-methyl-5-phosphono-3-hexenoic acid | 10.0 g |
|---|---|
| lactose | 207.0 g |
| modified starch | 80.0 g |
| magnesium stearate | 3.0 g |

Method: All the pulverulent constituents are sieved through a sieve having a mesh width of 0.6 mm. The active ingredient is then placed in a suitable mixer and mixed first with the magnesium stearate and then with the lactose and starch, until a homogeneous mixture is obtained. No. 2 gelatin capsules are each filled with 300 mg of this mixture, a capsule-filling machine being used.

Capsules that contain from 10 to 200 mg of one of the other disclosed compounds mentioned in Examples 1–59 are prepared in analogous manner.

EXAMPLE 46

Preparation of 10,000 tablets each containing 10 mg of the active ingredient of Example 6 and having the following composition:

| E-2-amino-4-methyl-5-phosphono-3-hexenoic acid | 100.00 g |
|---|---|
| lactose | 2535.00 g |
| corn starch | 125.00 g |
| polyethylene glycol 6000 | 150.00 g |
| magnesium stearate | 40.00 g |
| purified water | q.s. |

Method: All the pulverulent constituents are sieved through a sieve having a mesh width of 0.6 mm. The active ingredient is then mixed in a suitable mixer with the lactose, the magnesium stearate and half of the starch. The other half of the starch is suspended in 65 ml of water, and the suspension is added to a boiling solution of the polyethylene glycol in 260 ml of water. The resulting paste is added to the powders and the mixture is granulated, if necessary with the addition of more water. The granulate is dried overnight at 35°, forced through a sieve having a mesh width of 1.2 mm, and compressed to form tablets which have a breaking groove. Tablets that contain from 10 to 200 mg of one of the other disclosed compounds mentioned in Examples 1–44 are prepared in analogous manner.

What is claimed is:

1. A compound of formula I

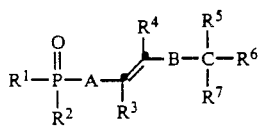

in which the carbon double bond is in the trans-configuration in relation to $R^3$ and $R^4$ or to A and B, and wherein $R^1$ represents hydroxy, lower alkoxy or hydroxy-lower alkoxy, $R^2$ represents hydrogen, alkyl, hydroxy, lower alkoxy or hydroxy-lower alkoxy, $R^3$ represents hydrogen, lower alkyl, halo-lower alkyl, lower alkoxy-lower alkyl, hydroxy-lower alkyl, phenyl-lower alkyl that is unsubstituted or substituted in the phenyl moiety, lower alkenyl, halogen, or unsubstituted or substituted phenyl, $R^4$ represents hydrogen, lower alkyl or unsubstituted or substituted phenyl, $R^5$ represents hydrogen or lower alkyl, $R^6$ represents carboxy, alkoxycarbonyl, alkoxycarbonyl substituted in a position higher than the α-position by amino, mono- or di-lower alkylamino, hydroxy or by lower alkanoyloxy, or phenyl-lower alkoxycarbonyl that is unsubstituted or substituted in the phenyl moiety, $R^7$ represents amino, mono- or di-lower alkylamino or lower alkanoylamino, A represents unsubstituted or lower alkylsubstituted α,ω-alkylene having from 1 to 3 carbon atoms, and B represents a bond, wherein the substituents of phenyl are selected from the group consisting of lower alkyl, hydroxy, lower alkoxy, halogen, amino, halo-lower alkyl, hydroxy-lower alkyl, amino-lower alkyl and nitro, or a pharmaceutically acceptable salt thereof.

2. Compounds of the formula I according to claim 1 in which $R^3$ represents hydrogen, lower alkyl or unsubstituted or substituted phenyl.

3. Compounds of the formula I according to claim 1 in which $R_6$ represents lower alkoxy carbonyl, alkoxycarbonyl or phenyl-lower alkoxycarbonyl substituted by lower alkyl, lower alkoxy, hydroxy or halogen.

4. Compounds of the formula I according to claim 1 in which $R^1$ represents hydroxy or lower alkoxy, $R^2$ represents hydrogen, alkyl, hydroxy or lower alkoxy, $R^3$ represents hydrogen, lower alkyl, phenyl, halophenyl, or phenyl-lower alkyl, $R^4$ and $R^5$ represent hydrogen or lower alkyl, $R^6$ represents carboxy, alkoxycarbonyl or hydroxy-lower alkoxycarbonyl, $R^7$ represents amino, mono-lower alkylamino, lower alkanoylamino or benzoylamino, A represents unsubstituted or lower alkyl-substituted α,ω-alkylene having from 1 to 3 carbon atoms or represents a bond and B represents methylene or a bond, and pharmaceutically acceptable salts thereof.

5. Compounds of the formula I according to claim 1 in which $R^1$ is hydroxy, $R^2$ represents hydrogen, alkyl or hydroxy, $R^3$ represents hydrogen, lower alkyl, phenyl-lower alkyl, phenyl or halophenyl, $R^4$ and $R^5$ represent hydrogen, $R^6$ represents carboxy or lower alkoxycarbonyl, $R^7$ represents amino, mono-lower alkylamino or lower alkanoylamino, A represents α,ω-alkylene having from 1 to 3 carbon atoms and B represents a bond, with the proviso that A is other than a bond when B represents a bond, and pharmaceutically acceptable salts thereof.

6. Compounds of the formula I according to claim 1 in which $R^1$ is hydroxy, $R^2$ represents hydrogen, lower alkyl or hydroxy, $R^3$ represents hydrogen or lower alkyl, $R^4$ and $R^5$ represent hydrogen, $R^6$ represents carboxy or lower alkoxycarbonyl, $R^7$ represents amino A represents α,ω-alkylene having from 1 to 3 carbon atoms, and B represents a bond, and pharmaceutically acceptable salts thereof.

7. Compounds of the formula I according to claim 1 in which $R^1$ and $R^2$ represent hydroxy, $R^3$ represents hydrogen or lower alkyl, $R^4$ and $R^5$ represent hydrogen, $R^6$ represents carboxy, $R^7$ represents amino, A represents methylene and B represents a bond, and the carboxylic acid lower alkyl esters and pharmaceutically acceptable salts thereof.

8. A compound claimed in claim 1 being E-2-amino-4-methyl-5-phosphono-3-pentenoic acid or a pharmaceutically acceptable salt thereof.

9. A compound claimed in claim 1 in the form of that enantiomer in which the C-atom carrying the group $R^7$ has R-configuration.

10. A compound claimed in claim 1 being (2R)-E-2-amino-4-methyl-5-phosphono-3-pentenoic acid or a pharmaceutically acceptable salt thereof.

11. A pharmaceutical composition containing a compound claimed in claim 1 together with a pharmaceutically suitable carrier material.

12. Method of treatment of diseases that respond to a blocking of NMDA-sensitive receptors, wherein a therapeutically effective amount of a compound claimed in claim 1 is administered to a warm-blooded organism in need of such treatment.

13. Method according to claim 12 for the treatment of cerebral ischaemia, muscular spasms (spasticity), convulsions (epilepsy), conditions of anxiety or manic conditions.

* * * * *